US008524213B2

(12) United States Patent
Leshchiner et al.

(10) Patent No.: US 8,524,213 B2
(45) Date of Patent: Sep. 3, 2013

(54) POLYMERIC MATERIALS, THEIR PREPARATION AND USE

(75) Inventors: Adelya K. Leshchiner, Cresskill, NJ (US); Paul Konowicz, Arlington, MA (US); Min-Yeh Grace Chang, Brookline, MA (US); Valentina Vasilyeva, Pomona, NY (US)

(73) Assignee: Genzyme Corporation, Cambridge, MA (US)

( * ) Notice: Subject to any disclaimer, the term of this patent is extended or adjusted under 35 U.S.C. 154(b) by 1433 days.

(21) Appl. No.: 11/475,850

(22) Filed: Jun. 26, 2006

(65) Prior Publication Data

US 2007/0036745 A1 Feb. 15, 2007

Related U.S. Application Data

(63) Continuation-in-part of application No. 11/026,388, filed on Dec. 30, 2004, now abandoned.

(60) Provisional application No. 60/533,429, filed on Dec. 30, 2003.

(51) Int. Cl.
*A61K 31/74* (2006.01)
*A61K 9/00* (2006.01)
*A61K 47/48* (2006.01)
*A61F 13/00* (2006.01)

(52) U.S. Cl.
USPC ............... 424/78.27; 424/422; 424/78.08; 424/400; 525/54.2

(58) Field of Classification Search
USPC ........... 424/78.27, 422, 78.08, 400; 525/54.2
See application file for complete search history.

(56) References Cited

U.S. PATENT DOCUMENTS

| 4,582,865 | A | 4/1986 | Balazs et al. |
| 4,605,691 | A | 8/1986 | Balazs et al. |
| 4,636,524 | A | 1/1987 | Balazs et al. |
| 4,713,448 | A | 12/1987 | Balazs et al. |
| 4,716,154 | A | 12/1987 | Malson et al. |
| 4,803,075 | A | 2/1989 | Wallace et al. |
| 5,143,724 | A | 9/1992 | Leshchiner et al. |
| 5,356,883 | A | 10/1994 | Kuo et al. |
| 5,827,937 | A | 10/1998 | Agerup |
| 6,383,344 | B1 | 5/2002 | Miller et al. |
| 6,475,795 | B1 * | 11/2002 | Turley et al. ................ 435/455 |
| 6,521,223 | B1 | 2/2003 | Calias et al. |
| 6,632,423 | B2 | 10/2003 | Jafari et al. |
| 6,685,963 | B1 | 2/2004 | Taupin et al. |
| 6,703,444 | B2 | 3/2004 | Zhao et al. |
| 6,921,819 | B2 | 7/2005 | Piron et al. |
| 2003/0148995 | A1 | 8/2003 | Piron et al. |
| 2004/0087488 | A1 * | 5/2004 | Parent et al. ................ 514/2 |
| 2005/0250939 | A1 | 11/2005 | Zhao |

FOREIGN PATENT DOCUMENTS

| EP | 0 244 987 | * | 4/1992 |
| EP | 0224987 | B1 | 4/1992 |
| EP | 0507604 | A2 | 7/1992 |
| EP | 0954323 | B1 | 1/2004 |
| EP | 0507604 | B1 | 7/2005 |
| WO | 00/01428 | A1 | 1/2000 |
| WO | 02/06350 | A1 | 1/2002 |
| WO | 2004/092222 | A2 | 10/2004 |

OTHER PUBLICATIONS

Scott et al, Proc. Natl. Acad. Sci. USA, vol. 96, pp. 4850-4855, Apr. 1999).*
Balazs et al., "An Automated Method for the Determination of Hexuronic Acids," Analytical Biochemistry, vol. 12, pp. 547-558 (1965).
Barnes et al., "An Introduction to Rheology," Elsevier (1989).
Bothner et al., "Limiting viscosity number and weight average molecular weight of hyaluronate samples produced by heat degradation," Int. J. Biol. Macromol., 10:287-291 (1988).
Chun et al., "Quantitation of Hyaluronic Acid in Tissues by Ion-Pair Reverse-Phase High-Performance Liquid Chromatography of Oligosaccharide Cleavage Products," Analytical Biochemistry, 171:197-206 (1988).
Guide for the Care and Use of Laboratory Animals, National Academy Press (1996).
Maccari et al., "High-performance capillary electrophoresis separation of hyaluronan oligosaccharides produced by Streptomyces hyalurolyticus hyaluronate lyase," Carbohydrate Polymers, 56:55-63 (2004).
"Polymers as Rheology Modifiers," edited by Schulz and Glass, ACS Symposium Series 462 (1991).
Shimada et al., "Degradation process of hyaluronic acid by Streptomyces hyaluronidase," J. Biochem., 88:1015-1023 (1980).

* cited by examiner

*Primary Examiner* — Blessing Fubara
(74) *Attorney, Agent, or Firm* — Fish & Richardson P.C.

(57) ABSTRACT

Disclosed are highly resilient and cohesive gels formed by the cross-linking of hyaluronan or hylan, their salts or derivatives thereof, using divinyl sulfone (DVS) as the cross-linking agent. Also disclosed are viscoelastic fluids containing alkyl-sulfone groups covalently attached to the backbone of the polymer, formed by the mono-functionalization of the cross-linking monomer DVS with hyaluronan and/or hylan. Mechanical properties such as values of hardness and cohesiveness are specified by the rheological properties of the gels. Also disclosed are methods for the preparation of such products. They have use in many applications as injectable and/or implantable devices and as drug delivery systems.

17 Claims, 6 Drawing Sheets

POLYMERIC MATERIALS, THEIR PREPARATION AND USE

CLAIM OF PRIORITY

This application is a continuation-in-part application of U.S. patent application Ser. No. 11/026,388 filed on Dec. 30, 2004 and published as US 2005/0142152A1 on Jun. 30, 2005 now abandoned, and which claims priority to U.S. patent application No. 60/533,429, filed on Dec. 30, 2003. Each of the above applications is incorporated herein by reference in its entirety.

TECHNICAL FIELD

The present invention relates to the production of materials such as gels, fluids and solids made by modifying natural and synthetic polymers with divinyl sulfone (DVS) and the unique chemical, physico-chemical and mechanical properties that these materials possess. The invention also relates to the use of these materials in many applications, e.g., in medical and surgical fields as injectable and/or implantable devices; drug delivery systems for large and small drug molecules and other therapeutic agents; and for cosmetic and topical applications.

BACKGROUND OF THE INVENTION

Hydrogels having exceptionally good bio-compatibility have been developed. These gels are based on hyaluronan, which is hyaluronic acid and its salts, and/or hylan and its salts. They are also based on hyaluronan or hylan cross-linked with DVS (FIGS. 1 and 2, see also U.S. Pat. Nos. 4,605,691 and 6,521,223), and/or cross-linked mixtures of hyaluronan with other polymers or low molecular weight substances (U.S. Pat. No. 4,582,865). Hylan A is a water soluble hyaluronan preparation chemically modified by covalent cross-linking with small amounts of an aldehyde, typically formaldehyde, while hylan B is hylan A further cross-linked by DVS (see U.S. Pat. No. 4,713,448). Gel slurries prepared from hyaluronan, chemically modified hyaluronan and hylan have also been described (U.S. Pat. No. 5,143,724). Such hydrogels may be used for drug delivery (U.S. Pat. No. 4,636,524) and other purposes in the medical field. However, these gels and gel slurries are non-elastic, non-cohesive, and non-adhesive.

SUMMARY OF THE INVENTION

The present invention provides in one aspect thereof, highly cohesive, adhesive and elastic gels of cross-linked hyaluronan and/or hylan or mixed gels of hyaluronan or hylan with other hydrophilic polymers capable of forming cross-links with DVS such as, but not limited to: glycosaminoglycans, e.g., chondroitin 4-sulfate and chondroitin 6-sulfate, chitosan; polyanionic polysaccharides, e.g., alkylcarboxy ether derivatives of cellulose and their salts, alginic acid and its salts, and polyhexuronic acids, e.g., pectin, polyglucuronic acid, and polymannuronic acid; other non-charged polysaccharides e.g., starch, glucomannans, galactomannans, pullulan, curdlan, innulin and cellulose and their hydroxyalkyl ether derivatives; polysaccharide gums, e.g., xanthan, Arabic, Acacia and Guar and their alkylcarboxy ether and hydroxyalkyl ether derivatives; and synthetic polymers, e.g., polyvinyl alcohol and polyethyleneimine. These gels are prepared from selected initial polymer concentrations (IPC) with specific concentrations of DVS or ratios of DVS to hyaluronan and/or hylan and/or a washing procedure effected in aqueous acidic media. In various embodiments of the invention, the term Initial Polymer Concentration, hereinafter "IPC," refers to the concentration by weight of the reactant under the starting reaction conditions. Where more than one starting polymer is used in the reaction, Initial Polymer Concentration refers to the total concentration by weight of the starting polymers under the starting reaction conditions. The term Final Polymer Concentration, hereinafter "FPC," refers to the concentration by weight of the modified polymer after all processing is complete. Where more than one starting polymer is used in the reaction, Final Polymer Concentration refers to the total concentration by weight of the modified polymers after all processing is complete.

In another aspect, the invention provides highly cohesive and elastic gels formed by modifying hyaluronan and/or hylan with DVS and a process for washing these materials in aqueous acidic medium (pH≦4.0). Such a washing process is important for enhancing the mechanical properties, cohesion and elasticity of the resultant materials.

In yet another aspect, the invention provides highly cohesive and elastic gels formed by modifying hyaluronan and/or hylan with DVS at low IPCs. These gels are more liquid-like in character and flow, and they adapt to the shape of the container in which they are stored.

In still another aspect, the invention provides highly cohesive and elastic gels which have a relatively high mechanical strength at relatively low IPC and show low flow characteristics. These materials retain the original shape of their former container after washing in dialysis tubing. In the above mentioned U.S. Pat. Nos. 4,582,865, 4,605,691, 4,636,524, 4,713,448 and 5,143,724, the preparation, properties and use of different kinds of gels formed from hyaluronan and/or hylan and other polysaccharides by cross-linking with DVS were described. However, the properties of the materials described in those patents are significantly different from those of the present invention. That is, the prior gels are hard, non-elastic and non-cohesive gels. These gels can easily be broken down into small and uniform particles during or after washing. By comparison, the gels of the present invention are elastic and cohesive, and have a strong tendency to re-form and behave as a single structure even after particulation.

It has also been discovered that two subgroups of cohesive gels of the present invention also possess singular structural features not possessed by the gels described in the prior art, as observed and quantified by HPLC analysis following digestion of the gels with hyaluronidase. In a first subgroup, the gels of the present invention exhibit a total modification of about 10% or less as determined by the method described in the examples 37 et seq. and a ratio of pendant groups to crosslinks of about 1.0 to about 0.10, or from about 0.08 to 0.10, or from about 0.10 to 0.70, or more preferably 0.10 to 0.40, as determined by the method described in the examples 37 et seq. The gels in this first subgroup are generally prepared from a bacterially derived hyaluronan or animal derived hylan in an initial concentration of at least 4% or more and preferably from about 4% to about 12% with a DVS:Pol ratio of less than 1/17 (0.059), and preferably from about 1/48 (0.021) to about 1/100 (0.01), followed by neutral or acid wash. In a second subgroup, the gels of the present invention exhibit a total modification of about 25% to about 35% and a ratio of pendant groups to crosslinks from about 1.3 to about 2.5 and preferably from about 1.5 to about 2.0, as determined by the method described in the examples 37 et seq. The gels in the second subgroup are generally prepared from a bacterially derived hyaluronan or animal derived hylan in an initial concentration of at least 1% or less and a DVS/pol ratio of 20 to 0.0025, or preferably an initial concentration of 0.9% to 0.15% and a DVS to polymer ratio of 10 to 0.025, or preferably yet an initial concentration of 0.5% to 0.25% and a DVS to polymer ratio of 6 to 4.

The invention provides methods for producing the above-described gels. The invention also provides a method of washing the gels in aqueous acidic media including salt solutions at pH≦4.0, preferably 2.0-3.0, but more preferably 2.3-2.8 followed by washing with an aqueous salt solution and a slow adjustment of pH to 4.5-6.5 with aqueous salt solutions alone or with the use of inorganic or organic bases. A final wash step with a buffered salt solution may be performed to bring the material to physiological pH (6.9-7.4) if desired.

The invention provides methods of using the gels alone or with a pharmaceutically acceptable carrier or excipient as injectable or implantable drug delivery systems such as anti-adhesion materials for both pre- and post-surgery in many kinds of open, laparoscopic, arthroscopic or other endoscopic surgeries, including but not limited to abdominal, gynecological, cardiac, spinal, neuro-, orthopedic, cranial, sinus and thoracic; in ophthalmic procedures such as, for example, phacoemulsification; for vitreal fluid replacement; as fillers for correcting soft tissue structural defects, tissue augmentation, and wound healing; for the treatment of scars and wrinkles in cosmetic surgery; for the creation of an embolism to treat arterial or venous aneurysms and to prevent blood flow to solid tumors. Pharmaceutically acceptable carriers or excipients can be chosen from, but are not limited to, saline, dimethyl sulfoxide, polyethylene glycol, hyaluronan, glycerol, and phospholipid solutions and emulsions. Additionally, the invention has utility for using the gels as delivery systems for biologically active materials including drugs, cells, proteins, DNA and vitamins and as materials for opthalmic and wound healing indications. Pharmaceutically active molecules or drugs can be chosen from, but are not limited to: non-steroidal anti-inflammatories such as Ibuprofen, Diclofenac and Piroxicam; anaesthetics such as Lidocaine and Bupivacaine; opioid analgesics such as Codeine and Morphine; anti-arrythmics such as Amiodarone, Propranolol and Sotalol; corticosteroids such as Dexamethasone and Prednisone; and antineoplastic agents such a Methotrexate, 5-fluorouracil and Paclitaxel; and anti-viral agents such as Acyclovir and Vidarabine.

Finally, the invention describes pharmaceutical compositions comprising the gels as devices for treatment of rheumatoid arthritis, for viscosupplementation in joints, for ophthalmic indications, for the treatment of osteoarthritis, and for wound healing.

The invention also provides methods for controlling the chemical, physico-chemical and mechanical properties of the polymeric materials of the invention by controlling the weight ratio of polymer to DVS during modification of the initial polymer and the washing conditions.

In a preferred embodiment, the invention provides a joint viscosupplementation device intended for use in the treatment of pain due to osteoarthritis, typically, but not necessarily, of the knee. The device is a pre-filled syringe having a single unit dosage of a sterile, non-pyrogenic composition comprising a swollen hydrogel and an unmodified fluid, both of which are derived, preferably, but not necessarily, from bacterially fermented sodium hyaluronate having a molecular weight greater than 1 MDa and having a pH and osmolality compatible with normal synovial fluid. The hydrogel component is preferably made from bacterially fermented sodium hyaluronate by reacting it with divinyl sulfone (DVS) under alkaline conditions to modify the sodium hyaluronate. The modified sodium hyaluronate is then washed with acidic saline and phosphate buffered saline (PBS) to remove impurities. The fluid component is a solution, preferably, of bacterially fermented sodium hyaluronate in phosphate buffered saline. The two components are combined in a gel:fluid ratio of about 80:20 by weight. The hydrogel component has a polymer content of 8.25±1.5 mg/ml, preferably 8.25±0.75 mg/ml. The fluid component has a polymer content of 2.25±1.0 mg/ml, preferably 2.25±0.25 mg/ml. The product thus has a total polymer content (modified and unmodified) of 10.5±2.5 mg/ml, preferably 10.5±1.0 mg/ml. The rheological properties of the product are: shear viscosity of 30-100 Pas (at 200 Hz); storage modulus (G' at 5 Hz) of 20-150 Pa; and a phase angle ($\delta$ at 5 Hz) of less than 35°.

In another preferred embodiment, the invention provides a joint viscosupplementation device intended for use in the treatment of pain due to osteoarthritis typically, but not necessarily, of the knee. The device is a pre-filled syringe having a single unit dosage of a sterile, non-pyrogenic composition comprising a swollen hydrogel which is derived, preferably, but not necessarily, from bacterially fermented sodium hyaluronate having a molecular weight greater than 1 MDa and having a pH and osmolality compatible with normal synovial fluid. The hydrogel is preferably made from bacterially fermented sodium hyaluronate by reacting it with divinyl sulfone (DVS) under alkaline conditions to modify the sodium hyaluronate. The modified sodium hyaluronate is then washed with acidic saline and phosphate buffered saline to remove impurities. The hydrogel in the final product has a polymer content of 8.25±1.75 mg/ml. The Theological properties of the product are: shear viscosity of 30-100 Pas (at 200 Hz); storage modulus (G' at 5 Hz) of 20-150 Pa; and a phase angle ($\delta$ at 5 Hz) of less than 35°.

DETAILED DESCRIPTION OF THE INVENTION

Figure 1:
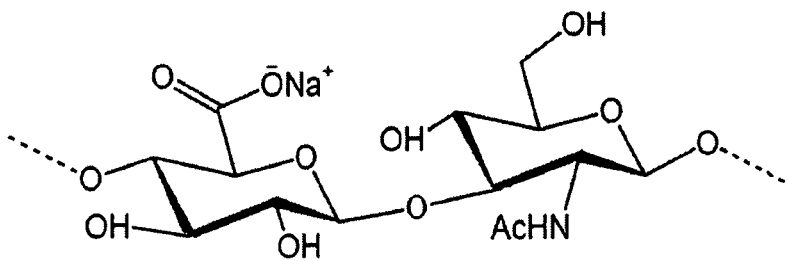
FIG. 1 shows sodium hyaluronate (hyaluronic acid; hyaluronan) structure.
Figure 2:
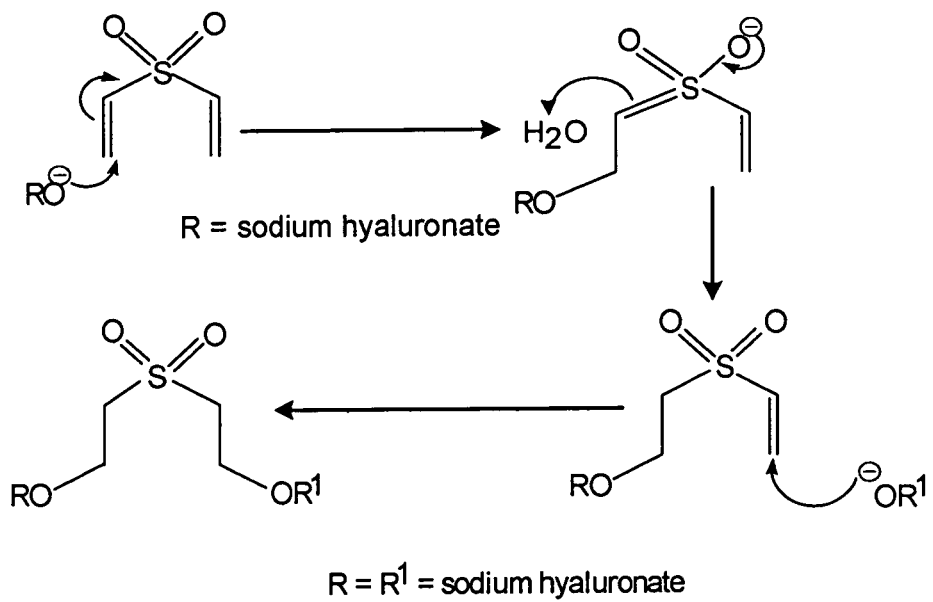
FIG. 2 shows the reaction scheme of sodium hyaluronate with DVS under basic conditions.
Figure 3:
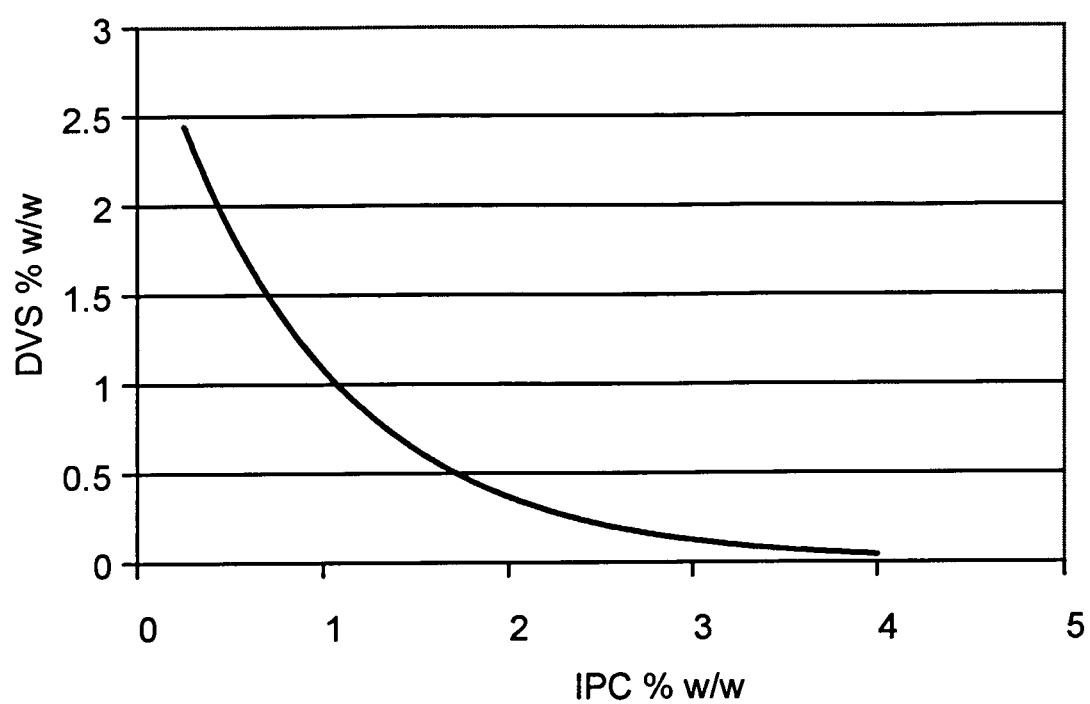
FIG. 3 is a graph showing the inversely proportional relationship of the ratio of DVS and IPC.

The present invention is based on the discovery that materials having unique and useful properties can be formed by modifying hyaluronan and/or hylan alone and/or with mixtures of other polymers, natural and synthetic, using DVS as a modifying reagent while controlling process parameters such as the IPC, ratio of initial reagents and further washing of the processed materials. The present invention provides gels having a uniform, single and resilient structure formed by the cross-linking reaction with DVS. These gels are not as easily broken down into small particles such as is the case with a brittle or fragile gel. These products give "putty" like or elastic materials and after being cut into sections, the particles tend to coalesce due to their highly cohesive properties. It has been observed that these types of cohesive, non-fragile gels can be obtained by using specific combinations of cross-linking reaction conditions, washing, IPC and the quantity of DVS. The mechanical properties of these gels are dependent upon all of these conditions, but most importantly, on the ratio of DVS to polymer (DVS:Pol) used and the acidic washing. The DVS:Pol ratio is inversely proportional to the IPC as shown in FIG. 3. Although not intending to be limited by any specific mechanism, it is believed that, the lower the polymer concentration, the higher the amount of DVS that is required for gel formation. This is in contrast to previously described gels, in which the DVS concentration was directly proportional to IPC.

In dilute solutions, polymer chains are separated by long distances and the interaction between polymer molecules is minimal. In this state solutions will freely flow as a consequence of external force (e.g., gravity or impulse from a stirrer). As the polymer concentration increases the number of molecules in solution increases, polymer chains are forced to come closer thereby increasing intermolecular interaction. In the case of extremely concentrated solutions, the chains are entangled with each other, their interaction increases, the viscosity increases drastically, and the solution begins to exhibit a transition from a concentrated solution to a gel. A gel will not readily deform or change its shape as a result of external forces. Covalent cross-linking is a way to significantly increase polymer chain interaction to form gels.

Storage (elastic) modulus (G') and loss (viscous) modulus (G") respectively represent the relative degrees a material can recover (elastic response) or flow (viscous response) as the rate of deformation (test frequency) changes. Both moduli are linear functions of the frequency. They have proven to be sensitive probes of the structure of polymer solutions and gels. Both G' and G" increase with increasing frequency, but one increases more quickly than the other. At the point where G'=G", this frequency is called cross-over frequency ($f_c$). The cross-over frequency decreases with increasing polymer molecular weight or concentration. For a polymer solution at low frequency, elastic stresses relax and viscous stresses dominate, and as a result G" is greater than G' at frequencies below $f_c$. In contrast, for a gel, there is no cross-over between G' and G", and G' is greater than G" across the frequency range. Unless otherwise specified, the test frequency is 0.04-7 Hz. Complex modulus, G*, reflects both the elastic component (G') and the viscous component (G"). It is calculated as the ratio of the stress amplitude to the strain amplitude of an oscillation test using a rheometer. The following relationships exist: G'=G* cos δ and G"=G* sin δ, wherein δ is phase angle. For a detailed review of physical properties of viscoelastic materials and methods of measuring these properties, see, e.g., "Polymers as Rheology Modifiers," edited by Schulz and Glass, ACS Symposium Series 462, 1991; "An Introduction to Rheology," H. A. Barnes, J. F. Hutton and K. Walters, Elsevier, 1989; and Bohlin Rheometer Application Notes MRK544-01, MRK556-01, and MRK573-01.

The characteristics of the gels of this invention made from low IPC are believed to be the result of reactions taking place in dilute solution. In dilute solutions the polymer molecules are not in close proximity to each other and there is a tendency for only one of the vinyl moieties of the modifying agent DVS to react with the polymer and form pendant groups, or for the DVS to be completely hydrolyzed and not to cross-link with another nearby polymer molecule. Therefore, the use of large amounts of modifying reagent with low IPC solutions is desirable in order to tailor the materials so as to have specific properties. The properties of the gels are also dependent upon the molecular weight (MW) of the starting polymer (as determined by intrinsic viscosity, H. Bothner, T. Waaler and O. Wik; *International Journal of Biological Macromolecules* [1988] 10, 287-91; or by mutiangle laser light scattering at MW<4 MDa), with low MW polymers requiring higher ratios of DVS:Pol to achieve similar properties to gels made from high MW polymers.

One preferred embodiment of the invention is an example of a class of elastic, polymeric gels produced by a process that uses purified, non-chemically modified hyaluronic acid or its salts as the starting material. This starting material may be prepared from animal tissue or from bacteria, provided that it is not chemically modified during the preparation thereof. The starting material is then subjected to reaction with divinyl sulfone to form a gel. The resulting gel is then subjected to an aqueous acidic (pH<4) wash step. A gel produced by this general process has the desirable mechanical properties of being soft, elastic and non-brittle. The term "hylastan" generally refers to the class of gels made by this process.

Suitable polymers may have an average MW of about 500 KDa to about 10 MDa, but preferably about 1.3 MDa to about 8 MDa. The low MW is preferably about 0.5 MDa to about 1.3 MDa, the medium MW is preferably about 1.3 MDa to about 2.7 MDa and the high MW is preferably about 2.7 MDa to about 10 MDa. The MW of sodium hyaluronate is preferably from about 0.5 MDa to about 4 MDa, and depending on the source, between about 0.5 MDa and about 1.3 MDa or about 1.3 MDa to about 2.7 MDa. The MW of hylan is preferably selected from about 3 MDa to about 10 MDa and most preferably about 3-6 MDa or about 4-8 MDa. The IPCs of the starting polymer may vary from 0.25% to 8% w/w. The ratio of DVS to polymer (DVS:Pol) may vary from 0.0025 to 0.05 w/w, preferably from 0.0025 to 0.025 w/w, or more preferably 0.0025 to 0.01 w/w when the IPC is in the range from 3 to 10% w/w, or more preferably in the range of 3-6% w/w. The ratio of DVS to polymer (DVS:Pol) may vary from 1.4 to 17.7 w/w when the IPC is in the range from 0.25-0.9% w/w. The reaction time for modification may also be varied, but is preferably ≦24 hours, and more preferably from 4 to 24 hours, depending on the IPC. At an IPC of ≦0.15% w/w for high MW polymer (such as Hylan A), gelation does not appear to occur, no matter what concentration of DVS is used because of the tendency of DVS to self-polymerize, hydrolyze or form pendant groups on the polymer as described above. At an IPC of 0.25-0.9% w/w, gel formation occurred and specific minimum DVS:hyaluronan ratios are required to form gels and give them the properties of cohesion and resilience as described above. Increasing the DVS:Pol ratio slightly causes the gels to become stronger, less elastic and less cohesive; whereas decreasing said ratio slightly causes them to be more liquid-like and more elastic. Thus, varying the DVS:Pol ratio allows the gels to be tailored to suit a specific purpose. The washing procedure after modification has an effect on the mechanical properties of the gels with acid washing contributing to the elastic and cohesive properties. The resultant acid-washed gels are softer (lower complex modulus values, G*), more elastic (higher yield strain) and less brittle than a gel (e.g., hylan B) prepared at similar polymer and DVS concentrations but not acid-washed. Gels with a high IPC have a tendency to become more elastic on heat treatment (during sterilization necessary to produce sterile medical products) in comparison to gels of hylan B (for example) with similar IPC which maintain their rigidity. Low IPC gels are very soft and elastic and heat treatment reduces the elasticity and viscosity.

Other suitable polymers may have an average MW of <500 KDa. The ultra low MW polymers may have MW from 30 KDa to 500 KDa, e.g., 30-100 KDa, 100-200 KDa, 200-500 KDa, 200-400 KDa, 200-300 KDa, 300-500 KDa, and 300-400 KDa.

Figure 4:
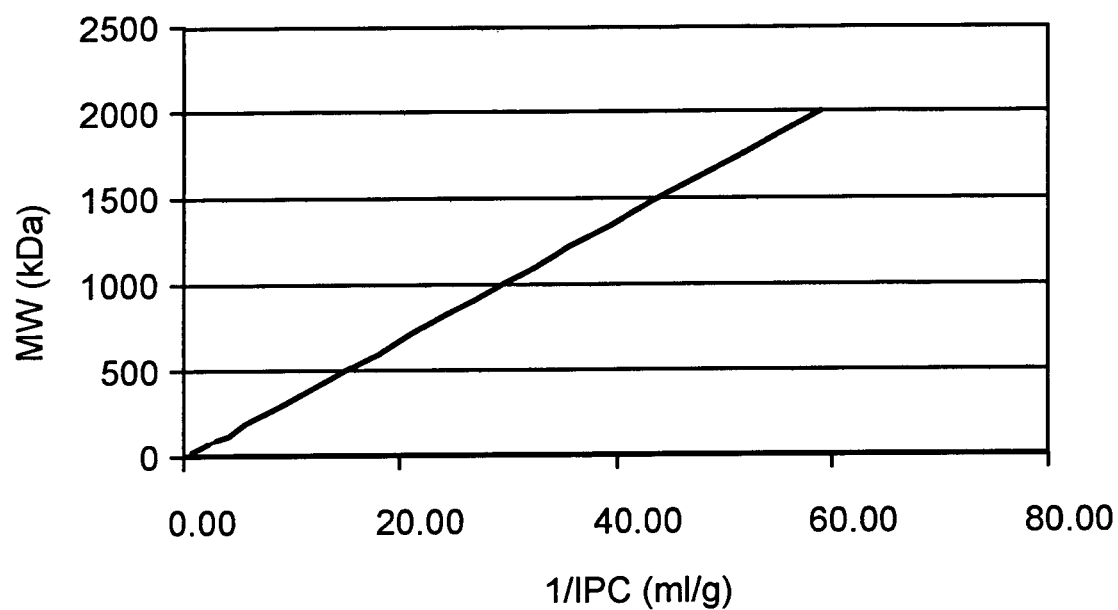
FIG. 4 is a graph showing the approximate directly proportional relationship between MW and 1/IPC for a fixed viscosity value.

To achieve desirable viscoelastic properties, the ultra low MW polymers may require a higher IPC as well as higher DVS:Pol ratios. For example, IPC for ultra low MW polymers may vary from 3 to 50% (w/w) or higher, depending on MW of the polymer with lower MW polymers requiring higher IPC. In general, MW of a polymer should be directly proportional to 1/IPC at a given viscosity value as shown in FIG. 4. Examples of IPC ranges for medium, low, ultra low MW polymers include, but are not limited to: 3%-8%, 3%-12%, 3%-15%, 3%-30%, 3%-50%, 8%-12%, 8-15%, 8%-30%, 8%-50%, 10%-12%, about 12%, 12%-30%, 12%-50%, and 20%-50%. DVS:Pol ratios for ultra low MW polymers may vary from 1:400 to 1:20 (w/w), or lower, depending on IPC. In general, the DVS:Pol ratio is inversely proportional to IPC as shown in FIG. 3. Examples of DVS:Pol ratio ranges for medium, low, ultra low MW polymers include, but are not limited to: about 0.0025 to about 20, about 0.005 to about 20, about 0.01 to about 20, 0.0025 to 17.7, 0.005 to about 17.7, 0.01 to about 17.7, about 0.0025 to about 10, about 0.005 to about 10, about 0.01 to about 10, about 0.1 to about 20, about 0.1 to about 10, about 1 to about 20, about 1 to about 10.

In some preferred embodiments, the gels of the invention have one or more of the following characteristics: (a) IPC 8-12%, preferably 10-12%; (b) HA MW 500-2500 KDa, preferably 500-600 KDa; (c) DVS:Pol ratio 1:200 to 1:15, preferably 1:100 to 1:15, e.g., 1:50 and 1:60; (d) FPC about 1% to 2.5%. The gels may be washed to equilibrium or otherwise. The gels may be acid-washed, or alternatively, be washed in neutral saline.

In one embodiment of the invention, the gels may be washed in aqueous acidic solutions, preferably, with aqueous acidic sodium, potassium, calcium, magnesium or ammonium chloride solutions, or mixtures thereof, and even more preferably, at 0.15 M sodium chloride concentration (physiological saline). The pH of the aqueous wash solution may be below or equal to 4.0, preferably pH 1.5-3, 2.0-3.0, but more preferably 2.3-2.8. The gels may then be washed in dialysis tubing (restricted wash) or without dialysis tubing (free wash). When the pH of the gels reaches a pH below or equal to 4.0, preferably pH 2.0-3.0, but more preferably 2.3-2.8. They may then be washed in aqueous salt solutions, preferably with aqueous sodium chloride solutions and more preferably with 0.15 M sodium chloride until the pH of the gel is 4.5-6.5. It was observed for gels prepared at the same IPC and DVS concentrations and washed in free wash conditions, that for gels washed in aqueous acidic solution followed by washing in aqueous neutral 0.15 M sodium chloride solution as described above, the swelling rate was reduced as compared to gels washed in neutral saline alone. By contrast, the use of dialysis tubing almost completely prevented swelling of the gels no matter how they were washed. It was also observed that the hyaluronan-based gels obtained from aqueous acid washing had a lower modulus and higher yield strain than hylan B gels prepared at similar concentrations and were therefore softer and more elastic. These materials are also highly cohesive and/or adhesive. They resist particulation and fragmentation during the washing procedure, unlike hylan B gels which can be clearly seen to fragment and particulate during the washing step. This suggests that the low pH achieved by aqueous acids, organic and inorganic acids and, in particular, mineral acids, preferably hydrochloric acid, altered and fixed the structure of the gel into a softer more elastic, cohesive and adhesive material. Storage of the gel for ≦24 hours in normal saline after acid wash, followed by a slow controlled adjustment of the gel to pH 4.5-6.5 maintains the structure imparted to the gels by the acid washing process. The pH of the gel may be slowly adjusted to 4.5-6.5 using organic or inorganic bases and/or buffers, particularly, in the case of non-equilibrium gels, or in the case equilibrium gels, the pH may be slowly adjusted to 4.5-6.5 by washing in neutral saline without the use of organic or inorganic bases and/or buffers. Gels may have a final wash with an aqueous buffer to bring the pH to physiological conditions if needed. As expected, those materials prepared from low IPCs have substantially lower swelling ability than materials prepared from those with higher IPCs. The preparation of the former materials requires the use of larger amounts of DVS and consequently more pendant alkylsulfone groups would be expected. In the case of materials with an IPC of 0.25% w/w and less, swelling within the dialysis tubing was minimal. Therefore, the combination of acidic washing, slow adjustment of the pH and a high degree of mono-functionalization of the polymer backbone with alkylsulfone groups all contribute to the low swelling properties of the gels.

It has also been further observed that gels prepared from polymers having an IPC from 0.25-0.9% w/w possess particular flow characteristics. They are more liquid-like (low viscosity) and adapt to the shape of the containers in which they are stored. Although these materials are relatively strong, they can be easily deformed, passed through a fine gauge needle like a liquid, and can flow into spaces between tissues. Thus, they are suitable for use as injectable products.

Generally, gels prepared from polymers having IPCs ≧1.0% w/w can be synthesized to be mechanically stronger, elastic and adhesive. These materials, when washed in dialysis tubing, conserve their shape upon removal from the tubing irrespective of the storage time in the containers. These gels tend to swell because of the higher IPC used and because they may contain more cross-links. However, the swelling rate may be controlled by the washing conditions, i.e., low pH as described above. The swelling can also be controlled by physical means such as using dialysis tubing and not washing the gel to equilibrium. Some of these gels may be useful for implants where slight swelling would be desirable. These gels also possess adhesive properties and some can easily stick to many different surfaces such as: skin, glass, plastic, cartilage, etc. These gels would be expected to remain in the positions in which they were placed longer than would be the case with more rigid gels. Polymer molecules at the surface of the gel are believed to have a greater degree of freedom than in a rigid gel and therefore are better able to interact with other gel particles and with the surfaces with which they come into contact.

In the case of gels made from polymers having 0.9% IPC and below, the higher content of alkylsulphonyl pendant groups in the gels may also have a role in allowing the gels to adhere to different surfaces. In the case of low IPC starting solutions, the amount of DVS can be controlled in such a way that the resultant gels are more cohesive or adhesive.

In one embodiment, the invention provides a process for preparing a cohesive gel comprising the steps of:
  a) providing a solution of at least one starting polymer (Pol) comprising a hyaluronan, a hylan, or a mixture thereof at an initial polymer concentration (IPC) of 0.25 w % to 50 w %;
  b) subjecting the at least one starting polymer to a reaction with divinyl sulfone (DVS); and
  c) washing the gel formed in step b with an aqueous solution having a pH≦4.

In related embodiments, the IPC is selected from the following ranges: 0.25 w % to 50 w %, 0.25 w % to 8 w %, 3 w % to 6 w %, 3 w % to 10 w %, 3 w % to 15 w %, 8 w % to 15 w %, 10 w % to 20 w %, and 9 w % to 20 w %.

In related embodiments, the ratio of divinyl sulfone to polymer (DVS:Pol) (w:w) is selected from about 0.0025 to about 17.7. In a further embodiment, the ratio of divinyl sulfone to polymer (DVS:Pol) (w:w) is selected from about 0.005 to about 17.7. In yet another embodiment, the ratio of divinyl sulfone to polymer (DVS:Pol) (w:w) is selected from about 0.01 to about 17.7.

In further embodiments, the invention provides a process for preparing a cohesive gel comprising the steps of:
  a) providing a solution of at least one starting polymer (Pol) comprising a hyaluronan, a hylan, or a mixture thereof at an initial polymer concentration (IPC) of >8 w % (e.g., 8.1, 8.5, 9, 9.5, 10, 11, 12, 13, 15, and 20 w %) to 25, 30, 40, or 50 w %;
  b) subjecting the starting polymer to a reaction with divinyl sulfone (DVS) to form a gel, wherein the DVS:Pol (w:w) ratio may be selected from about 0.0025 to about 0.033, from about 0.05 to about 0.033, or from about 0.01 to about 0.033.

Optionally, the process may further comprise the step of washing the gel formed in step b with an aqueous solution having a pH≦4.

For gels with an IPC of higher than 8 w %, the average MW of the starting polymer is selected from 30 KDa to 5 MDa, preferably from 30 KDa to 4 MDa, from 500 KDa to 3 MDa, or from 500 KDa to 2.5 MDa. In such embodiments, the IPC may be selected, from the following ranges, e.g., 8%-15%, 8%-30%, 10%-12%, about 12%, 12%-30%, 12%-50%, and 20%-50%.

In further embodiments, the invention provides a process for preparing a cohesive gel comprising the steps of:
  a) providing a solution of at least one starting polymer (Pol) comprising a hyaluronan, a hylan, or a mixture thereof at an initial polymer concentration (IPC) of 0.25 w % to 50 w % (e.g., 3 w % to 8 w %, 0.25 w % to 8 w %, 3 w % to 6 w %, 3 w % to 10 w %, 3 w % to 15 w %, 8 w % to 15 w %, 10 w % to 20 w %, 9 w % to 20 w %, 8% to 30%, 10 w % to 12 w %, about 12 w %, 12 w % to 30%, 12 w % to 50 w %, and 20 w % to 50 w %;
  b) subjecting the starting polymer to a reaction with divinyl sulfone (DVS) to form a gel at a ratio of divinyl sulfone to polymer (DVS:Pol) (w:w) selected from about 0.025 to 0.05, from about 0.0025 to about 0.033, from about 0.05 to about 0.033, or from about 0.01 to about 0.033.

Optionally, the process may further comprise the step of washing the gel formed in step b with an aqueous solution having a pH≦4.

In further embodiments, the invention also provides a process for preparing a cohesive gel comprising the steps of:
  a) providing a solution of at least one starting polymer (Pol) comprising a hyaluronan, a hylan, or a mixture thereof at an initial polymer concentration (IPC) of 0.25 w % to 0.9 w % (e.g., 0.25 w % to 0.5 w %, 0.3 w % to 0.8 w %, 0.5 w % to 0.8%, about 0.5 w %); and
  b) subjecting the starting polymer to a reaction with divinyl sulfone (DVS).

In certain embodiments, the ratio of DVS:Pol (w:w) is selected from about 1.4 to about 17.7, from about 2 to 15, from about 5 to about 15, from about 2 to about 10. Optionally, the process may further comprise the step of washing the gel formed in step b with an aqueous solution having a pH≦4.

In related preferred embodiments, the average MW of the starting polymer is selected from 500 KDa to 6 MDa. Optionally, such gels may be acid-washed. In various embodiments, the average molecular weight (MW) of one of the at least one starting polymer is selected from about 30 KDa to about 500 KDa, e.g., 30-100 KDa, 100-200 KDa, 200-500 KDa, 200-400 KDa, 200-300 KDa, 300-500 KDa, and 300-400 KDa. In these or other embodiments, the ratio of divinyl sulfone to polymer (DVS:Pol) (w:w) is selected from about 0.0025 to about 20, e.g., about 0.05 to about 20, 0.01 to about 20, about 0.0025 to about 0.033, 0.05 to about 0.033, and 0.01 to about 0.033.

The process for making gels that include washing the gels with an aqueous solution having a pH≦4, may comprise the step of adjusting the pH of the gel from ≦4 to physiological pH with a buffered saline solution. Alternatively, the process further comprises the step of adjusting the pH of the gel from ≦4 to about 4.5 to 6.5 with a buffered saline solution. In another embodiment, the invention provides a process as described where in the acid wash step (step c) the gel is washed to a pH about 2.0 to 3.0. The invention also provides a process wherein the cross-linking step (step b) is conducted at a pH≧9. The invention further provides a process wherein step b is allowed to proceed for ≦24 hours.

In some embodiments, the gel is washed to non-equilibrium in dialysis tubing.

Generally, the invention also provides a process wherein the average molecular weight of at least one starting polymer is about ≦10 MDa. In a further embodiment, the average molecular weight (MW) of at least one starting polymer is selected from about 0.5 MDa to about 4 MDa. In a preferred embodiment, the at least one starting polymer is a hyaluronan. In yet another embodiment, the average molecular weight (MW) of one of the at least one starting polymer is selected from about 3 MDa to about 10 MDa. In still another embodiment, the average MW of the polymer is <500 KDa. In a preferred embodiment, the at least one starting polymer is a hylan. In some embodiments, the average MW of the starting polymer is from about 30 KDa to about 500 KDa.

In further embodiments, the invention provides a gel with a polymer (e.g., hyaluronan, preferably bacterially fermented HA) content of 8.25±1.75 mg/ml and the rheological properties of the product as follows: shear viscosity of 30-100 Pas (at 200 Hz); storage modulus (G' at 5 Hz) of 20-150 Pa, e.g., about 80 Pa; and a phase angle (δ at 5 Hz) of less than 35°, e.g., about 20 Pa.

In some embodiments, the invention provides a composition, comprising a mixture of the gel ("gel component") with a polymer solution ("fluid component"). In particular embodiments, the gel and fluid components are mixed at a ratio of 80:20 by weight. In such embodiments, the polymer (HA) content in the gel is 8.25±1.5 mg/ml, preferably 8.25±0.75 mg/ml, while the fluid component has a polymer content of 2.25±1.0 mg/ml, preferably 2.25±0.25 mg/ml. (The composition thus has a total polymer content (modified and unmodified) of 10.5±2.5 mg/ml, preferably 10.5±1.0 mg/ml.) Alternatively, the components can be mixed at a ratio from 60:40 to 90:10, e.g., 70:30, 75:25, and 85:15. The rheological properties of the composition are as follows: shear viscosity of 30-100 Pas (at 200 Hz); storage modulus (G' at 5 Hz) of 20-150 Pa; and a phase angle (δ at 5 Hz) of less than 35°.

The invention further provides a device, which is a pre-filled syringe having a single unit dosage of a sterile, non-pyrogenic composition comprising the gel component with or without the fluid component, prepared according to any of the methods disclosed herein.

The invention also provides a process wherein the cross-linking step (step b) is conducted in the presence of a biologically active material. The biologically active material may comprise a pharmacological drug, a protein, a DNA, a vitamin or other desirable biologically active material.

The invention further provides a process comprising the step of mixing the gel at physiological pH with a biologically active material. The biologically active material may comprise a pharmacological drug, a protein, a DNA, a vitamin, cells or other biologically active material. The biologically active material may be admixed with a gel that has been produced by the methods of the invention and/or be present with the starting material.

The invention also provides a process wherein the solution of the starting polymer comprises a hyaluronan, a hylan, or a mixture thereof and another polymer selected from glycosaminoglycans, polyanionic polysaccharides, non-charged polysaccharides, polysaccharide gums, polyalcohols and polyamines.

The invention also provides for a gel prepared according to any of the above-described processes of the invention. In a further embodiment, the invention provides a pharmaceutical composition comprising the gel and a pharmaceutical excipient.

In still another embodiment, the invention provides a method of treating a medical condition in a patient by administering to a patient in need thereof the pharmaceutical composition comprising the gel.

In a preferred embodiment, the medical condition is osteoarthritis (OA) and the composition is administered in a joint space, such as, for example, a knee, shoulder, temporo-mandibular and carpo-metacarpal joints, elbow, hip, wrist, ankle, and lumbar zygapophysial (facet) joints in the spine. The viscosupplementation may be accomplished via a single or multiple intraarticular injections administered over a period of weeks into the knee or other afflicted joints. For example, a human subject with knee OA may receive one, two, or three injections of about 2, 3, 4, 5, 6, 7, 8, 9, 10 ml or more per knee. For other joints, the administered volume can be adjusted based on the size on the joint.

In another embodiment, the composition is used to create an embolism.

In an additional embodiment, the medical condition or treatment is for the prevention or inhibition of the formation of postsurgical adhesion and the composition is administered to the site of a surgical incision. Alternatively, the medical condition or treatment is for the prevention or inhibition of postsurgical adhesion and the composition is administered to a tissue distant from the site of a surgical incision. In a preferred embodiment, the composition is administered through an endoscope.

In additional embodiments, the compositions of the invention can be used as a dermal filler, for example, for treating wrinkles and skin or other tissue volume defects, or for vocal cord expansion.

In the foregoing description, examples and claims which follow, divinyl sulfone to polymer ratios (DVS:Pol) are reported on a w/w basis unless indicated otherwise. The weights of sodium hyaluronate or soluble hylan fibers (sodium salt) were adjusted to discount their water content. Medium and high MW bacterially fermented sodium hyaluronate had MWs of about 1.7 MDa and about 2.7 MDa, respectively. Medium MW sodium hyaluronate was obtained from Shiseido Corporation, Japan. High and Low MW sodium hyaluronate were obtained from Genzyme Corporation, Cambridge, Mass. The low and ultra low MW polymers was produced using a gamma irradiation method as described in U.S. Pat. No. 6,383,344. Soluble hylan fibers (sodium salt) had a MW of about 6 MDa and were obtained from Genzyme Biosurgery, Ridgefield, N.J. and were prepared according to U.S. Pat. No. 4,713,448. Neutral saline refers to 0.15 M sodium chloride solution at a pH of about 6-7. For free washing, the amount of hydrochloric acid (HCl) used for washing was calculated as that necessary to bring the neutral saline wash solution to pH≦4.0, preferably pH 2.0-3.0 or 1.5 to 3.0 but more preferably pH 2.3-2.8, and then corrected for the moles of acid needed to neutralize the sodium hydroxide used in the reaction mixture and then convert the salt form of the polysaccharide to the acid form, e.g., sodium hyaluronate to hyaluronic acid. For restricted washing, the gel was washed with aqueous acidic saline solution, which is neutral saline to which HCl has been added until the pH was below or equal to 4.0, preferably pH 2.0-3.0. Restricted washing was continued preferably until the gel had a pH of 2.3-2.8. Phosphate buffered saline (PBS) had a pH of 7.3-7.4, unless otherwise indicated. Gels were washed at room temperature, unless indicated otherwise. The term physiological pH is intended to mean a pH range of about 6.9 to 7.5. The strength of the gel samples, soft or hard, was determined on the basis of their phase angles δ and complex modulus G* with low phase angles and high complex modulus values indicating strong gels. The elastic and cohesive properties of the gels were determined by their yield strain with high yield strain values indicating elastic and cohesive gels. Visual observations and manual manipulations of the gels also gave an indication of their adhesive and cohesive properties. Hyaluronan and hylan concentrations were determined by hexuronic acid assay using an automated carbazole method (Analytical Biochem 1965, 12, 547-558). All dialyzed samples used dialysis tubing with a molecular weight cut off of 12-14 KDa.

Throughout this application, various publications are referenced. The teachings of those publications are hereby incorporated by reference in their entireties. The present invention is described in more detail in the following Examples which are given merely by way of illustration and are not intended to limit the scope of the invention as set forth in the claims.

Tables referred to in the Examples are located at the end. In the following Examples where salt has been added, IPC is calculated as the concentration of the polymer in sodium hydroxide solution before the addition of a viscosity modifier such as, e.g., NaCl, or other salts, preferably biocompatible salts. Unless otherwise specified, the terms "%" and "w %" in reference to IPC are used interchangeably.

EXAMPLE 1

0.75% IPC with Bacterially Fermented Sodium Hyaluronate Medium MW

This example illustrates the preparation of a gel with an IPC of 0.75% and the DVS:Pol ratio of 2:1.

To medium MW bacterially fermented sodium hyaluronate powder (about 1.7 MDa, 5.30 g) was added sterile water 525.7 g in a sterile reactor vessel and mixed on an orbital shaker for 18 hours at 4° C. To this solution, at room temperature, was added sterile filtered 1M NaOH solution (60.00 mL) affording a polymer solution having NaOH at 0.1 M concentration. To the polymer solution was added DVS (7.60 mL) with mechanical mixing (300-500 rpm) and the mixture was stirred for 25 minutes at room temperature. The reaction mixture was placed into dialysis tubing and then stored at room temperature for 4 hours affording a gel. The gel was then washed against sterile neutral saline (10.0 L) containing HCl solution (7.70 mL) until the pH was between 2.3-2.8. The gel was then washed extensively with neutral saline until the pH was about 5.1. The gel was then washed extensively with 12 L portions of neutral saline to which has been added 13.5 mL of neutral saline containing 0.5M NaHCO$_3$ until the pH was between 7.0 and 7.4. The gel was then removed. The final yield of gel was 607.1 g and a FPC of 0.72%. A portion of the gel was autoclaved at 131° C. for 10 minutes. The rheological data shown in Table 1 and observation indicated that the gel was elastic and soft and cohesive.

EXAMPLE 2

0.5% IPC with Hylan Fibers

This Example illustrates the preparation of gel with an IPC of 0.5% and a DVS:Pol ratio of 4:1.

To a 0.75% solution of hylan sodium salt (about 6 MDa, 265.6 g) was added sterile water (133.1 g) and then mixed on a roller apparatus for about 18 hours at room temperature. Sterile filtered 1 M NaOH solution (45.00 mL) was added and the fluid mixed on a Turbula T2F end over end shaker for 10 minutes. Then DVS (2.50 mL) was added and mixing was continued for 30 minutes more. The reaction mixture was then transferred into dialysis tubing and stored at room temperature for 4 h. The resulting gel was washed with neutral saline containing 12 M HCl solution (6.50 mL) until the pH was about 2.3-2.8 and then washed extensively with 3.0 L portions of neutral saline until the pH was about 6.0-6.5. The gel was then washed extensively with 3.0 L portions of neutral saline to which has been added 4.0 mL of neutral saline containing 0.5M NaHCO$_3$ until the pH was about 7. The gel was adhesive, and cohesive, but rather soft with a FPC of 0.45%. Based on elemental analysis data the sulfur content was 3.56%. A portion of the gel was autoclaved at 131° C. for 10 minutes. The rheological data shown in Table 1 and observation indicated that the gel was liquid-like, elastic and soft and cohesive.

EXAMPLE 3

0.38% IPC with Hylan Fibers

This Example illustrates the preparation of a gel with an IPC of 0.38% and a DVS:Pol ratio of 6:1.

To hylan fibers (sodium salt) (1.34 g) was added sterile water (261.9 g) and the mixture was mechanically stirred at room temperature for 18 hours. To the polymer solution, at room temperature, was added 1 M NaOH solution (30.00 mL) affording a polymer solution having NaOH at 0.1 M concentration. The polymer solution was mechanically stirred at 300-500 rpm for 10 minutes. To this polymer solution was added DVS (1.940 mL) suspended in de-ionized water (0.880 mL). The reaction mixture was stirred for approximately 30 minutes at room temperature and then additional DVS (3.800 mL) was added followed by mixing for another 30 minutes. The reaction mixture was poured into dialysis tubing using a funnel for a restricted wash and stored at room temperature for 3 hours in a closed container with a small amount of saline to provide some humidity and prevent the tubing from drying out. The resulting gel was then dialyzed against 0.15 M saline which had been acidified to a pH of about 2.5 using HCl solution, until the pH of gel reached 2.7. The gel was then dialyzed against neutral saline until the pH was about pH 6.5. The gel had a FPC of 0.35%. A portion of the gel was autoclaved at 131° C. for 10 minutes. The rheological data shown in Table 1 and observation indicated that the gel was soft, cohesive and quite elastic, but more liquid-like than gel-like in character.

EXAMPLE 4

0.25% IPC with Hylan Fibers

This Example illustrates the preparation of a gel with an IPC of 0.25% and a DVS:Pol ratio of 8:1.

Hylan fibers (sodium salt) (0.144 g) were dissolved by shaking in deionized water (42.00 mL) on an orbital shaker for about 24 h. To the polymer solution was added 1 M NaOH solution (5.00 mL) and the polymer solution was stirred on an overhead mixer. To the polymer solution was added a suspension of DVS (0.880 mL) in deionized water (1.875 mL) and it was mixed for 2 hours at room temperature. The color of the product changed from a light to dark gray over the course of 2 hours. The reaction mixture was stored overnight at ~4° C., resulting in a gel. The gel was then transferred into dialysis tubing for restricted wash and washed against 0.15 M saline solution acidified to a pH of about 2.5 with HCl solution over the course of two days. It was then extensively washed against neutral saline for 5-7 days. Rheological analysis (Table 1) and observation showed that the product was an elastic and relatively soft gel.

EXAMPLE 5

0.15% IPC with Hylan Fibers

This Example illustrates the preparation of a material with an IPC of 0.15% and a DVS:Pol ratio of 17.7:1.

To hylan fibers, (sodium salt) (0.231 g) was added a 0.1 M NaOH solution (97.52 g) and the mixture was stirred at ~500 rpm for ~80 minutes. To the polymer solution was then added DVS (2.250 mL) with vigorous mechanical mixing for 5 minutes. The reaction mixture slowly changed color from peach to milky white over the course of ~4 hours. The reaction mixture was stored overnight at room temperature. The reaction mixture still appeared to be a liquid after overnight storage and it was then transferred to a dialysis tube for restricted washing. The mixture was washed on an orbital shaker at ~120 rpm against 4.0 L of neutral saline to which was added 12.0 mL of 2 M HCl to achieve an acidic saline wash having a pH of 2.5. After ~8 hours, the acidic saline wash solution was exchanged for 4.0 L of fresh acidic saline wash prepared as described and the reaction mixture was stored at 4° C. for about 72 hours. After approximately 72 hours storage the product did not appear to have gelled and had separated into two phases a colorless upper phase and a milky white lower phase.

EXAMPLE 6

4.0% Bacterially Fermented Sodium Hyaluronate Medium MW

This Example illustrates the preparation of a gel at an IPC of 4% and a DVS:Pol ratio of 1:17.

Medium MW bacterially fermented sodium hyaluronate (8.42 g) was added to a beaker containing a 0.2 M NaOH solution (190.60 g) and mechanically stirred (500-750 rpm) at room temperature for about 90 minutes. To the polymer solution was slowly added DVS (0.400 mL) dissolved in isopropyl alcohol (IPA) (0.600 mL) and the mixture was stirred for an additional 15 minutes. (The IPA was used to help disperse the small volume of DVS in the larger volume of polymer solution—any suitable water miscible diluent may be chosen.) The reaction mixture was poured into a 23×18 cm Pyrex® glass dish, covered and stored for four hours, affording a gel. The gel was then transferred to a glass container containing neutral saline (4.8 L) to which had been added 2 M HCl (36.00 mL) and shaken on an orbital shaker at room temperature for about 24 hours. The pH of the gel was measured (2.7-2.8) and then the gel was washed in neutral saline (10.0 L) for about 24 hours. The pH of the gel was measured (3.3) and it was then washed in 0.025 M phosphate buffered saline solution (3.0 L) for 24 hours. The final yield of gel was 953.8 g with a FPC of 0.81%. A portion of the gel was autoclaved at 126° C. for 10 minutes. The rheological data shown in Table 1 and observation indicated that the gel was somewhat elastic and cohesive, but relatively hard. Based on elemental analysis data the sulfur content was 0.95%.

EXAMPLE 7

4.8% IPC Bacterially Fermented Sodium Hyaluronate Medium MW

This Example illustrates the preparation of a gel with an IPC of 4.8% and a DVS:Pol ratio of 1:48.

To a 0.2 M NaOH solution (200 ml) was slowly added medium MW bacterially fermented sodium hyaluronate (10.52 g) with rapid mechanical stirring giving a polymer solution with an IPC of 4.8%. After 90 minutes, a solution of DVS (0.170 mL) dissolved in IPA (0.830 mL) was slowly added by pipette (5×~0.2 mL) over one minute to the polymer solution. The reaction mixture was stirred for 15 minutes and then poured into a Pyrex® tray (23×18×6.6 cm) and sealed with a plastic cover. The reaction mixture was stored at room temperature for a further 3.75 hours. The resulting gel was then transferred to a glass container and free washed with neutral saline (3.0 L) to which had been added 2M HCl solution (16.50 mL) and with agitation on an orbital shaker at room temperature for about 24 hours. The gel was removed, the pH was recorded (2.8), and it was then washed with neutral saline (10.0 L) on an orbital shaker. After approximately 24 hours, the saline was drained using a sieve and the gel washed with 0.025 M phosphate buffered saline (3.5 L) at a pH of 7.6 for about 24 hours. The gel (1.19 Kg and pH 7.2) was then removed from the wash. The FPC was 0.53%. A sample of the product was autoclaved at 121° C. for 15 minutes. The Theological data shown in Table 1 and observation indicated that the gel was elastic, cohesive and soft.

EXAMPLE 8

4.8% IPC with Bacterially Fermented Sodium Hyaluronate High MW

This Example illustrates the preparation of a gel with an IPC of 4.8% and a DVS:Pol ratio of 1:96.

To a 0.2M NaOH solution (189.63 g) was slowly added high MW bacterially fermented sodium hyaluronate (10.27 g) with rapid mechanical stirring giving a polymer solution with an IPC of 4.8%. After 90 minutes, a solution of DVS (0.080 mL) in IPA (0.920 mL) was slowly added by pipette (5×~0.2 mL) over one minute to the polymer solution. The reaction mixture was stirred for 15 minutes and was then poured into a Pyrex® tray (23×18×6.5 cm) and sealed with a plastic cover. The reaction mixture was stored at room temperature for 4 hours affording a gel and then transferred to a glass container containing neutral saline (3.0 L) to which was added 2 M HCl solution (36.00 ml). It was then agitated on an orbital shaker at room temperature for 24 hours. The wash solution was drained using a sieve and the gel was removed. The pH of the gel was recorded (2.4) and it was then washed with neutral saline (7.5 L) on an orbital shaker for 4 hours. The pH of the gel was slowly adjusted to 5.0-6.5 by the addition of 1 M NaOH solution (21.50 mL) over the course of 24 hours to the wash. The saline was then drained and the gel washed with 0.01 M PBS solution (3.0 L) at pH 7.4 for 7.5 hours. A portion of the material was autoclaved at 126° C. for 10 minutes. The rheological data shown in Table 1 and observation indicated that the gel was elastic, cohesive and soft.

EXAMPLE 9

5.6% IPC with Bacterially Fermented Sodium Hyaluronate High MW

This Example illustrates the preparation of a gel with an IPC 5.6% and a DVS:Pol ratio of 1:48.

To 0.2M NaOH (187.60 g) was added NaCl (11.70 g) with stirring until dissolved. High MW bacterially fermented sodium hyaluronate (12.30 g) was added with rapid mechanical stirring, which was then continued for 120 minutes, giving a polymer solution with an IPC of 5.6%. To the polymer solution was added a solution of DVS (0.200 mL) dissolved in IPA (0.800 mL), slowly added by pipette (5×~0.2 mL) over one minute. After 2-3 minutes of stirring, the mixture was poured into a Pyrex® tray (23×18×6.5 cm) and sealed with a plastic cover. The reaction mixture was stored at room temperature for 4 hours affording a gel. It was then transferred to a glass container containing 0.15 M saline (3.0 L) to which was added 2 M HCl solution (36.00 mL) and agitated on an orbital shaker at room temperature for 24 hours. The wash solution was drained using a sieve and the gel was removed. The pH of the gel was recorded (2.2) and it was then washed with neutral saline (7.5 L) on an orbital shaker for 4 hours. The pH of the gel was slowly adjusted to 5.0-6.5 by the addition of 1 M NaOH solution (21.50 mL) over the course of 24 hours to the wash. The saline was drained and the gel washed with 0.01 M PBS (3.0 L) at pH 7.4 for 8-24 hours. The final yield was 1008.5 g at a FPC of 1.0%. The concentration of a portion of the material was adjusted to 0.75% by adding 0.01 M PBS solution, and was autoclaved at 126° C. for 10 minutes. The rheological data shown in Table 1 and observation indicated that the gel was elastic, cohesive and soft.

EXAMPLE 10

5.6% Bacterially Fermented Sodium Hyaluronate High MW

This Example illustrates the preparation of a gel with an IPC 5.6% and a DVS:Pol ratio of 1:96.

To a 0.2 M NaOH solution (186.90 g) was added NaCl (11.70 g) with stirring until dissolved. High MW bacterially fermented sodium hyaluronate (12.30 g) was added with rapid mechanical stirring which was continued for 120 minutes giving a polymer solution with an IPC of 5.6%. To the polymer solution was added a solution of DVS (0.100 mL) in IPA (0.900 mL) slowly added by pipette (5×~0.2 mL) over one minute. After 2-3 minutes of stirring the mixture was poured into a Pyrex® tray (23×18×6.5 cm) and sealed with a plastic cover. The reaction mixture was stored at room temperature for 4 hours affording a gel and then transferred to a glass container with a solution containing NaCl (13.80 g) and 2M HCl (39.50 mL) in de-ionized water (3.0 L) and agitated on an orbital shaker at room temperature for 24 hours. The wash solution was drained using a sieve and the gel was removed. The pH was recorded (2.1) and the gel was then washed with neutral saline (7.0 L) on an orbital shaker for 4 hours. The pH of the gel was slowly adjusted to 5.0-6.5 by the addition of 1 M NaOH solution (22.50 mL) over the course of 24 hours to the wash. The wash solution was drained and the gel washed with 0.01 M PBS solution (3.0 L) at pH 7.4 for 8-24 hours. The final yield of gel was 883.5 g with a FPC of 0.88%. The concentration of a portion of the gel was adjusted to 0.74% by adding 0.01 M PBS solution. This material was autoclaved at 126° C. for 10 minutes. The rheological data shown in Table 1 and observation indicated that the gel was elastic, cohesive and soft.

EXAMPLE 11

6.0% IPC with Bacterially Fermented Sodium Hyaluronate High MW

This Example illustrates the preparation of a gel with a 6% IPC and a DVS:Pol ratio of 1:48.

To 0.2 M NaOH (186.75 g) was added NaCl (11.70 g) with stirring until dissolved. High MW bacterially fermented sodium hyaluronate (13.00 g) was added with rapid mechanical stirring which was continued for 120 minutes giving a polymer solution with an IPC of 6.0%. To the polymer solution was added a solution of DVS (0.210 mL) in IPA (0.790 mL), added by pipette (5×~0.2 mL) over one minute. After 2-3 minutes of stirring, the reaction mixture was poured into a Pyrex® tray (23×18×6.5 cm) and sealed with a plastic cover. It was stored at room temperature for 4 hours affording a gel and then transferred to a glass container containing neutral saline (3.0 L) to which had been added 2 M HCl solution (37.90 ml) and agitated on an orbital shaker at room temperature for about 24 hours. The wash solution was drained using a sieve and the pH of the gel was recorded (2.4). The gel was then washed with neutral saline (7.0 L) for 4 h and then was slowly adjusted to 5.0-6.5 by the addition of 1 M NaOH solution (21.50 mL) over the course of 24 hours to the wash. The saline was then drained through a sieve and the gel was washed with 0.01 M phosphate buffered saline (3.0 L) at pH 7.6 for about 8-24 hours. The final yield of gel was 1008.2 g with a FPC of 0.97%. The concentration of a portion of this material was adjusted to 0.68% by the addition of 0.01 M PBS solution. This material was autoclaved at 126° C. for 10 minutes. The rheological data shown in Table 1 and observation indicated that the gel was elastic, cohesive and soft.

EXAMPLE 12

6.0% IPC with Bacterially Fermented Sodium Hyaluronate High MW

This Example illustrates the preparation of a gel with a 6% IPC and an DVS:Pol ratio of 1:96.

To a 0.2 M NaOH solution (186.71 g) was added NaCl (11.79 g) with stirring until dissolved. High MW bacterially fermented sodium hyaluronate (13.17 g) was added with rapid mechanical stirring which was continued for 120 minutes giving a polymer solution with an IPC of 6.0%. To the polymer solution was added DVS (0.105 mL) dissolved in IPA (0.900 mL) slowly by pipette (5×~0.2 mL) over about one minute. After another 2-3 minutes of stirring the reaction mixture was poured into a Pyrex® tray (23×28×6.5 cm) and sealed with a plastic cover. It was stored at room temperature for 4 hours affording a gel and then transferred to a glass container containing neutral saline (3.0 L) to which had been added 2 M HCl solution (36.00 mL) and agitated on an orbital shaker at room temperature for about 24 hours. The gel was removed, the pH recorded (2.2) and then washed with neutral saline (7.0 L) on an orbital shaker for approximately 4 hours. The pH of the gel was slowly adjusted to 5.0-6.5 by the addition of 1 M NaOH solution over the course of 24 hours to the wash. The saline was then drained through a sieve and the gel washed with 0.01 M PBS solution (3.0 L) at pH 7.6 for 4 hours. The final yield was 1040.4 g with a FPC of 1.12%. The concentration of a portion of the gel was adjusted to 0.74% by the addition of 0.01 M PBS solution. This material was autoclaved at 126° C. for 10 minutes. The rheological data shown in Table 1 and observation indicated that the gel was elastic, cohesive and soft.

EXAMPLE 13

8.0% IPC with Bacterially Fermented Sodium Hyaluronate Medium MW

This Example illustrates the preparation of a gel with an 8% IPC and a DVS:Pol ratio 1:100.

To 0.2 M NaOH (91.58 g) was added NaCl (5.85 g) with stirring until dissolved. Medium MW bacterially fermented sodium hyaluronate (8.35 g) was added with rapid mechanical stirring which was continued for 120 minutes giving a polymer solution with an IPC of 8.0%. To the polymer solution was added a solution of DVS (0.068 mL) in IPA (0.932 mL), slowly added by pipette (5×~0.2 mL) over one minute and stirring was continued for another 2-3 minutes. The reaction mixture was stored at room temperature for 4 hours affording a gel and then transferred to a glass container containing neutral saline (5.96 g NaCl in 1.8 L) to which had been added 2 M HCl solution (23.80 mL) and then agitated on an orbital shaker at room temperature for about 24 hours. The wash solution was drained using a sieve and the pH of the gel recorded (2.4). It was then washed with neutral saline (4.5 L) on an orbital shaker for 4 hours and then the wash solution was drained. The pH of the gel was slowly adjusted to 5.0-6.5 by first washing the gel in neutral saline for 8 hours, draining the wash solution and then using neutral saline (4.5 L) containing 1 M NaOH solution (15.00 mL). A final wash step was performed with 0.01 M PBS solution (3.0 L). The final yield of gel was 882.7 g at a FPC of 0.81%. This material was autoclaved at 126° C. for 10 minutes. The rheological data shown in Table 1 indicated that the gel was elastic, cohesive and soft.

EXAMPLE 14

3% IPC with Hylan Fibers

This Example illustrates the preparation of a gel with a 3% IPC and a DVS:Pol ratio of 4:17.

To a 0.1 M NaOH solution (192.00 g), with rapid mechanical stirring, were added hylan fibers (sodium salt) (6.60 g) and stirring was continued for 2 hours until dissolved. To the polymer solution was added DVS (1.200 mL) with rapid mechanical stirring. The reaction mixture was stirred for approximately 2 minutes at high speed, then poured into a Pyrex® tray (23×18×6.5 cm) and sealed with a plastic cover. The reaction mixture was stored at room temperature for 2 hours affording a gel and then transferred to a glass container with a solution of neutral saline (3.0 L). The gel was then agitated on an orbital shaker at room temperature for about 24 hours. The wash solution was then drained using a sieve and another wash using neutral saline (3.0 L) was performed. The wash solution was changed 5 times over 3 days. A final wash in 0.01 M PBS solution (3.0 L) for 24 h was performed in order to ensure the gel pH was 6.9-7.4 prior to autoclaving. The final yield of gel was 821.0 g with a FPC of 0.57%. The concentration of a portion of the gel was adjusted to 0.49% by addition of PBS and this sample was autoclaved at 126° C. for 10 minutes. The Theological data as shown in Table 2 and observation indicated that the gel was typical of hylan B gel and was non-elastic, non-cohesive and hard.

EXAMPLE 15

3% IPC with Hylan Fibers

This Example illustrates the preparation of a gel with a 3% IPC and a DVS:Pol ratio of 4:17.

To a 0.2 M NaOH solution (192.00 g), with rapid mechanical stirring, were added hylan fibers (sodium salt) (6.60 g) and stirring was continued for 2 hours until dissolved. To the polymer solution was added DVS (1.200 mL) with mechanical stirring. The reaction mixture was stirred for about 2 minutes then poured into a Pyrex® tray (23×18×6.5 cm) and sealed with a plastic cover. The reaction mixture was then stored at room temperature for 4 hours affording a gel and then transferred to a glass container containing neutral saline (3.0 L) to which had been added 2 M HCl solution (23.10 mL). The gel was then agitated on an orbital shaker at room temperature. After about 19 hours the saline was drained using a sieve and the gel weight (286.7 g) and pH (2.8) were noted. The gel was washed again with neutral saline (3.0 L) and shaken for 4 hours on an orbital shaker. 1 M NaOH solution was then added slowly to the wash solution over the course of several hours to increase the pH of the gel to 4.5-6.5. After approximately 21 hours the wash solution was drained and the gel weight (626.2 g) and pH (6.8-7.5) were noted. The gel was then transferred into 0.01 M PBS solution (3 L) and washed for about 17 hours. The final yield of gel was 761.7 g with a FPC of 0.64%. The concentration of a portion of the material was adjusted to 0.52% by addition of 0.01 M PBS solution. This material was autoclaved at 126° C. for 10 minutes. The rheological data shown in Table 2 and observation indicated that the gel was softer and more elastic and more cohesive than the gel of Example 14.

EXAMPLE 16

1% IPC with Hylan Fibers

This Example illustrates the preparation of a gel with a 1% IPC and a DVS:Pol ratio of 5:1.

To a 0.1M NaOH solution (93.90 g), with rapid mechanical stirring, were added hylan fibers (sodium salt) (1.10 g) and stirring was continued for 1 hour until dissolved. To the polymer solution was added DVS (5 aliquots of 0.850 mL each) with rapid mechanical stirring. The reaction mixture was stirred for 10 minutes at high speed. The beaker was covered and stored at room temperature for 2 hours affording a gel. The gel was then transferred to a glass container with of neutral saline (1.8 L). The gel was then agitated on an orbital shaker at room temperature for about 24 hours. The wash solution was then drained using a sieve and more neutral saline (4.5 L) was added to the gel. The wash solution was changed 10 times (4.5 L each) over 7 days. A final wash in 0.01 M PBS solution (3.0 L) was performed in order to ensure that the gel pH was 6.9-7.4 prior to autoclaving. The final yield of gel was 166.1 g with an FPC of 0.42%. A portion of the gel was autoclaved at 126° C. for 10 minutes. The rheological data as shown in Table 2 and observation indicated that the gel was not very elastic or cohesive and relatively hard.

EXAMPLE 17

0.9% IPC with Hylan Fibers

This Example illustrates the preparation of a gel with a 0.9% IPC and a DVS:Pol ratio of 5:1.

To a 0.2 M NaOH solution (94.00 g), with rapid mechanical stirring, was added hylan fibers (sodium salt) (1.00 g) and stirring was continued for 1 hour until dissolved. To the polymer solution was added DVS (5 aliquots of 0.765 mL each) with rapid mechanical stirring. The reaction mixture was stirred for 10 minutes at high speed. The beaker was covered and stored at room temperature for 4 hours affording a gel. The gel was then transferred to a glass container containing neutral saline (1.8 L) to which had been added 2 M HCl solution (15.10 mL). The gel was then agitated on an orbital shaker at room temperature for about 24 hours. The wash solution was then drained using a sieve, the pH recorded (2.3) and more neutral saline (4.5 L) was added to the gel. The gel was allowed to wash for about 4.5 hours and then the wash was drained. The wash was continued with neutral saline (4.5 L) to which had been added 1 M NaOH solution (2.00 mL). After 16-18 hours the wash solution was drained and the gel was washed in 0.01M PBS solution (2 washes of 20.0 L each) for about 48 hours in order to ensure that the gel pH was 6.9-7.4 prior to autoclaving. The final yield of gel was 155.9 g with an FPC of 0.49%. A portion of the gel was autoclaved at 126° C. for 10 minutes. The rheological data shown in Table 2 and observation indicated that the gel was softer and more elastic than the gel of Example 16.

EXAMPLE 18

1% IPC with Hylan Fibers

This Example illustrates the preparation of a gel with a 1% IPC and a DVS:Pol ratio of 1.4:1.

To a 0.1 M NaOH solution (97.55 g) with rapid mechanical stirring, was added hylan fibers (sodium salt) (1.10 g) and stirring was continued for 1 hour until dissolved. To the polymer solution was added DVS (1.200 mL) with rapid mechanical stirring. The reaction mixture was stirred for 10 minutes at high speed, and the mixture transferred to dialysis tubing. The reaction mixture was stored at room temperature in a closed container for 2 hours affording a gel. The gel was then transferred to a glass container containing neutral saline (3.0 L). A gap or headspace equivalent to about 10% of the volume was left in the tubing to allow for swelling. The gel was then agitated on an orbital shaker at room temperature for 24 hours. After 24 hours the gel had swelled to fill the tube and was exerting a high hydrostatic pressure on the tube. The tube was lengthened to allow more headspace for the gel to swell. The gel was extensively washed with neutral saline until the pH was 6.5-7.0. The final yield of gel was 98.9 g with an FPC of 0.73%. The concentration of a portion of the gel was adjusted to 0.50% with 0.01 M PBS solution and it was autoclaved at 126° C. for 10 minutes. The rheological data as shown in Table 2 and observation indicated that the gel was less elastic, less cohesive and harder than the gel from Example 19 below.

EXAMPLE 19

0.9% IPC with Hylan Fibers

This Example illustrates the preparation of a gel with a 0.9% IPC and a DVS:Pol ratio of 1.4:1.

To 0.2 M NaOH solution (97.74 g), with rapid mechanical stirring, was added hylan fibers (sodium salt) (1.00 g) and stirring was continued for 2 hours until dissolved. To the polymer solution was added DVS (1.070 mL) with rapid mechanical stirring. The reaction mixture was stirred for 3 minutes at high speed, and the gel transferred to dialysis tubing and stored in a closed container at room temperature for 4 hours, affording a gel. The gel was then transferred in the tubing to a glass container containing neutral saline (3.0 L) to which had been added 2 M HCl solution (15.10 mL). A small gap or headspace of about 10% of the tube volume was left for swelling. The glass container with gel was then agitated on an orbital shaker at room temperature for 24 hours. Only minimal swelling was observed in contrast to Example 18. The wash solution was drained, the pH of the gel recorded (2.3) and a neutral saline (4.0 L) wash was performed. The gel was allowed to wash for about 3 hours. 1 M NaOH solution (2.60 mL) was then added to the wash. The gel was washed for an additional 26.5 hours and then the wash solution was drained. The wash solution was then changed to 0.01 M PBS solution (4.0 L) to ensure that the gel pH was 6.9-7.4 prior to autoclaving at 126° C. for 10 minutes. Only a slight swelling of the gel was observed, in marked contrast to Example 18. The final yield of gel was 89.0 g with a FPC of 0.78%. The concentration of a portion of the material was adjusted to 0.49% with PBS and autoclaved at 126° C. for 10 minutes. The rheological data shown in Table 2 indicated that the gel was softer, more elastic and cohesive than that of Example 18.

EXAMPLE 20

4.0% IPC with Bacterially Fermented Sodium Hyaluronate Medium MW

This Example illustrates the preparation of a gel with a 4% IPC and a DVS:Pol ratio of about 1:15.

To a 0.1 M NaOH solution (95.54 g) was added Medium MW bacterially fermented sodium hyaluronate (4.21 g) with rapid mechanical stirring which was continued for 120 minutes until dissolved giving a polymer solution with an IPC of 4.0%. To the polymer solution was added a solution of DVS (0.225 mL) in IPA (0.750 mL) with rapid stirring for 2-3 minutes. The reaction mixture was stored at room temperature for 1 hour affording a gel and was then transferred to a glass container with neutral saline (1.8 L) and agitated on an orbital shaker at room temperature for 24 hours. The wash solution was drained using a sieve and the gel was then washed with neutral saline (4.0 L) on an orbital shaker for 24 hours. The gel was washed extensively with neutral saline until the pH was about 6.5-7.0. The swelling rate of the gel in saline was low. The saline was then decanted. Final gel yield was (562.5 g) with a FPC of 0.63%. A portion of the material was autoclaved at 126° C. for 10 minutes. The rheological data shown in Table 2 and observation indicated that the gel was harder less elastic and less cohesive than the gel in Example 6.

EXAMPLE 21

8.0% IPC with Bacterially Fermented Sodium Hyaluronate Medium MW

This Example illustrates the preparation of a gel with an 8% IPC and a DVS:Pol ratio of 2:35. To a 0.2 M NaOH solution (90.63 g) was added NaCl (5.85 g) with stirring until dissolved. Medium MW bacterially fermented sodium hyaluronate (8.40 g) was added with rapid mechanical stirring which was continued for 120 minutes until dissolved giving a polymer solution with an IPC of 8.0%. To the polymer solution was added a solution of DVS (0.390 mL) in IPA (0.610 mL), by pipette (5x~0.2 mL) over one minute. The reaction mixture was mixed at high speed for 2-3 minutes and was stored at room temperature for 4 hours affording a gel. It was then transferred to a glass container containing neutral saline (3.0 L) to which had been added 2M HCl solution (21.00 mL) and agitated on an orbital shaker at room temperature for about 25 hours. The wash solution was drained using a sieve, the pH of the gel recorded (2.2) and the gel washed with more neutral saline (4.0 L) on an orbital shaker for 17 hours. The pH of the gel was slowly adjusted to 5.0-6.5 by the addition of 1 M NaOH solution (15.00 mL) to the wash over the course of 7 days. The gel was then washed with 0.01 M PBS solution (2.0 L) for about 24 hours and then with additional 0.01 M PBS solution 4.0 L for 7 days, when the pH of the gel was 7.4. The final yield of gel was 416.3 g with an FPC of 1.73%. The concentration of a portion of the material was adjusted to 1.5% with 0.01 M PBS solution. A portion of both materials was autoclaved at 126° C. for 10 minutes. The rheological data as shown in Table 2 and observation indicated that the gel was very hard and non-elastic and non-cohesive, but could be slightly diluted without phase separation.

EXAMPLE 22

8.0% IPC with Bacterially Fermented Sodium Hyaluronate Medium MW

This Example illustrates the preparation of a gel with an 8% IPC and a DVS:Pol ratio of 1:15.

To a 0.1 M NaOH solution (90.91 g) was added medium MW bacterially fermented sodium hyaluronate (8.56 g) with rapid mechanical stirring which was continued for 120 minutes until dissolved giving a polymer solution with an IPC of 8.0%. To the polymer solution was added DVS (0.450 mL) with rapid stirring. The reaction mixture was mixed at high speed for 2-3 minutes and was stored at room temperature for 2 hours affording a gel. It was then transferred to a glass container with neutral saline (1.8 L) and agitated on an orbital shaker at room temperature for 24 hours. The gel was washed extensively with 4.5 L portions of neutral saline over the course of 9 days during this time the gel was observed to fracture and particulate easily during the washing step. The swelling rate of the gel in saline was low. The final yield of gel was 400.1 g with a FPC of 1.76%. A portion of the material was autoclaved at 126° C. for 10 minutes. The rheological data shown in Table 2 and observation indicated that the gel was very hard, non-elastic and non-cohesive. The concentration of the material could not be adjusted lower without phase separation in comparison to the gel of Example 21.

EXAMPLE 23

0.75% IPC with High MW Sodium Hyaluronate and 0.75% Chondroitin 6 Sulfate

This Example illustrates how a gel may be prepared where the IPC of the sodium hyaluronate and chondroitin 6 sulfate are each 0.75% and the DVS:sodium hyaluronate ratio is 2:1.

To high MW sodium hyaluronate (0.75 g) and chondroitin 6-sulfate (0.75 g) may be added de-ionized water (87.00 g) and the mixture is mechanically stirred at room temperature for about 24 h. To the mixed polymer solution, at room temperature, is added 1 M NaOH solution (10.00 mL) affording a mixed polymer solution having NaOH at 0.1 M concentration. The polymer solution is mechanically stirred at high speed for 10 minutes. To this polymer solution is added DVS (1.275 mL). The reaction mixture is stirred for approximately 30 minutes at high speed. The reaction mixture is poured into dialysis tubing and is stored at room temperature for 3 hours, a gel is the result. The gel is then dialyzed against 0.15 M saline (3.0 L) which is acidified to a pH of about 2.5 using HCl solution. It is washed until the pH of gel is about 2.3-2.8. The wash solution is then drained and the gel is then dialyzed extensively against 3.0 L portions of neutral saline until the pH is about pH 6.5. A final wash in 0.01 M PBS solution (3.0 L) is performed to ensure the pH of the gel is about 7.4 prior to autoclaving.

EXAMPLE 24

0.75% IPC with High MW Sodium Hyaluronate and 0.75% Polyvinyl Alcohol

This Example illustrates how a gel may be prepared where the IPC of the sodium hyaluronate and polyvinyl alcohol are each 0.75% and the DVS:sodium hyaluronate ratio is 2:1.

To hot (60° C.) de-ionized water (87.00 g) is added polyvinyl alcohol (MW ~100 KDa, 0.75 g) and the mixture is mechanically stirred for about 2 h. The polymer solution is allowed to come to room temperature and then medium MW sodium hyaluronate (0.75 g) is added with mechanical stirring for about 24 h. To the mixed polymer solution is added 1 M NaOH solution (10.00 mL) affording a mixed polymer solution having NaOH at 0.1 M concentration. The mixed polymer solution is mechanically stirred at high speed for 10 minutes. To this polymer solution is added DVS (1.275 mL). The reaction mixture is stirred for approximately 30 minutes at high speed. The reaction mixture is poured into dialysis tubing and is stored at room temperature for 3 hours, a gel is the result. The gel is dialyzed against 0.15 M saline (3.0 L) which is acidified to a pH of about 2.5 using HCl solution. It is washed until the pH of gel is about 2.3-2.8. The wash solution is then drained and the gel is then dialyzed extensively against 3.0 L portions of neutral saline until the pH is about pH 6.5. A final wash in 0.01 M PBS solution (3.0 L) is performed to ensure the pH of the gel is about 7.4 prior to autoclaving.

EXAMPLE 25

0.9% IPC with High MW Sodium Hyaluronate and 0.9% Carboxymethyl Cellulose

This Example illustrates how a gel may be prepared where the IPC of the sodium hyaluronate and carboxymethyl cellulose are each 0.75% and the DVS:sodium hyaluronate ratio is 1.4:1.

To high MW sodium hyaluronate (0.90 g) and carboxymethyl cellulose (0.90 g) is added de-ionized water (86.90 g) and the mixture is mechanically stirred at room temperature for about 24 h. To the mixed polymer solution, at room temperature, is added 1 M NaOH solution (10.00 mL) affording a mixed polymer solution having NaOH at 0.1 M concentration. The polymer solution is mechanically stirred at high speed for 10 minutes. To this polymer solution is added DVS (1.105 mL). The reaction mixture is stirred for approximately 30 minutes at high speed. The reaction mixture is poured into dialysis tubing and is stored at room temperature for 3 hours, a gel is the result. The gel is dialyzed against 0.15 M saline (3.0 L) which is acidified to a pH of about 2.5 using HCl solution. It is washed until the pH of gel is about 2.3-2.8. The wash solution is then drained and the gel is then dialyzed extensively against 3.0 L portions of neutral saline until the pH is about pH 6.5. A final wash in 0.01 M PBS solution (3.0 L) is performed to ensure the pH of the gel is about 7.4 prior to autoclaving.

EXAMPLE 26

3.0% IPC Bacterially Fermented Sodium Hyaluronate Medium MW and 1.0% IPC Sodium Alginate This Example illustrates the preparation of a gel may be prepared with an IPC of 4.0% and a DVS:Pol ratio of 1:24.

To a 0.2 M NaOH solution (191.70 g) is slowly added medium MW bacterially fermented sodium hyaluronate (6.00 g) and sodium alginate (2.00 g) with rapid mechanical stirring for 90-120 minutes to give a polymer solution with an IPC of 3.0% sodium hyaluronate and 1.0% sodium alginate. A solution of DVS (0.210 mL) dissolved in IPA (0.790 mL) is slowly added by pipette (5x~0.2 mL) over one minute to the polymer solution. The reaction mixture is stirred for 15 minutes and is then poured into a Pyrex® tray (23×18×6.6 cm) and sealed with a plastic cover. The reaction mixture is stored at room temperature for a further 225 minutes. The resulting gel is then transferred to a glass container with neutral saline (3.0 L) containing 2 M HCl solution (27.80 mL) and is agitated on an orbital shaker at room temperature for about 24 hours. The wash is then drained using a sieve, the pH is recorded (2.8) and the gel is then extensively washed with 3.0 L portions of neutral saline on an orbital shaker until the pH is 5.0-6.5. The gel is then washed with 0.01 M phosphate buffered saline (3.0 L) for about 24 hours.

EXAMPLE 27

Acid Washed Gel Admixtures with Water Soluble Drugs for Drug Delivery

To a gel of Example 9 (50.00 g, 0.75% FPC) under aseptic handling conditions (laminar flow hood) may be added: a 0.01 M PBS solution of a non-steroidal anti-inflammatory drug such as Diclofenac (16.80 mL, 9 mg/mL); a local anesthetic such as Bupivacaine hydrochloride (35.00 mL, 5 mg/mL); an antineoplastic such as Methotrexate (5.00 mL, 25 mg/mL) or an anti-arrythmic such as Propranolol hydrochloride (5.00 mL, 25 mg/mL). The gel with drug is mixed on a Turbula T2F mixer at a speed of 23 min$^{-1}$ and at room temperature for about 24 h. The admixture is then frozen and lyophilized to a dry foam-like material. The gel is reconstituted to a FPC of 0.75% by adding sterile 0.01 M PBS or sterile 0.15 M saline (49.63 g) and mixing on a Turbular T2F mixer for about 24 h. The material may be terminally sterilized by autoclaving if desired.

EXAMPLE 28

Acid Washed Gel Admixtures with Water Insoluble Drugs for Drug Delivery

To a gel of Example 9 (50.00 g, 0.75% FPC) under aseptic handling conditions (laminar flow hood) may be added: a solution of a steroidal anti-inflammatory drug such as Dexamethasone (5.00 mL, 25 mg/mL); an antineoplastic such as Paclitaxel (25.00 mL, 5 mg/mL); or an anti-arrhythmic such as amiodarone (5.00 mL, 5 mg/mL) in a dipolar aprotic solvent such as dimethylsulfoxide. The gel and drug solution may be mixed on a Turbula T2F mixer at a speed of 23 $min^{-1}$ and at room temperature for about 24 h. The admixture is then placed into sterile dialysis tubing and extensively dialyzed against 2.0 L portions of neutral saline under aseptic conditions, or precipitated from an excess of ethanol or other water miscible solvent in which the drug is not soluble and dried under vacuum. The gel is reconstituted to a FPC of 0.75% by adding sterile 0.01 M PBS or sterile 0.15 M saline (49.63 g) and mixing on a Turbular T2F mixer for about 24 h. The material may be terminally sterilized by autoclaving if desired.

EXAMPLE 29

Use of Acid Washed Gels in Adhesion Reduction

An evaluation of the adhesion reduction potential of Examples 6 and 7 using a rat cecal-abrasion model was conducted. The study was performed in accordance with the NIH guidelines as described in the *Guide for the Care and Use of Laboratory Animals*, National Academy Press, 1996. The cecum was abraded four times on the ventral and dorsal surfaces with a mechanical abrading device, which permits operator-independent, controlled abrasion over a defined area, and then returned to its anatomical position within the abdominal cavity. Animals were assigned into three groups, one surgical control and two treatment groups consisting of 10 animals each. Each side of the cecum in the two treatment groups received 1.5 $cm^3$ of gels prepared according to Examples 6 and 7 evenly distributed over the cecal surface for a total of 3 $cm^3$. The surgical control group did not receive any further treatment after abrasion. On day seven post-operatively the animals were evaluated for adhesion formation by grade.

| Group | Mean Incidence ± SEM | % Animals with no adhesions |
|---|---|---|
| Surgical Control | 1.9 ± 0.3 | 11 |
| Example 6 | 0.3 ± 0.2§ | 70* |
| Example 7 | 0.1 ± 0.1§ | 89* |

§$p < 0.05$ vs control group Wilcoxon Rank Sum Analysis
*$p < 0.05$ vs control group Chi Square Analysis

EXAMPLE 30

Use of Acid-Washed Gels as Joint Viscosupplements

An evaluation of the safety of intra-articular injection of test articles including gels prepared according to Example 31 in Hartley guinea pig knees was conducted. This is an appropriate model for the evaluation of safety within the joint. The study was performed in accordance with the NIH guidelines as described in the *Guide for the Care and Use of Laboratory Animals*, National Academy Press, 1996. The guinea pigs were divided into groups of six animals each, including one control group. The groups received three injections at weekly intervals in the femoropatella joint of the rear left. Both rear legs were assessed for joint width using calipers at the level of the joint (tibial plateau) pre-injection and the first day post-injection for each injection. The animals were also evaluated grossly for gait abnormalities. A histological analysis was also conducted to determine any joint soft tissue inflammation. There was no difference between the control and the test article for the variables evaluated (range of motion, knee width at the day of necropsy). Histological analysis showed no significant inflammatory or degenerative changes associated with the injection of gels into guinea pig knees.

EXAMPLE 31

5.25% Bacterially Fermented Sodium Hyaluronate High MW

This Example illustrates the preparation of a gel with an IPC of 5.25% and a DVS:Pol ratio of 1:96.

175.4 g of NaCl was added to 2829.6 g of 0.2 M NaOH solution, and stirred until dissolved. High MW bacterially fermented sodium hyaluronate (163.8 g, 5% LOD) was added to the mixture with rapid mechanical stirring in four portions (41.0, 41.1, 40.8 and 40.9 g) at 20-minute intervals. The mixing continued for a total of 120 minutes. The resulting polymer solution had an IPC of 5.25%. A DVS solution (1.38 mL of DVS and 6.52 mL of IPA) was slowly added by pipette to the polymer solution in four equal portions of 2 mL at approximately 10 second intervals. After approximately 1 minute of stirring, the reaction mixture was poured into a large polypropylene tray and covered with a plastic cover. The reaction mixture was stored at room temperature for 4 hours, resulting in a gel. The gel was cut into eight roughly equal pieces and then transferred to a large polypropylene container containing 44 Kg of 0.15 M sodium chloride solution and 850 mL 1 M HCl. The gel pieces were agitated by bubbling filtered nitrogen through the solution at a rate of approximately 0.5-3.5 Lpm. After approximately 18 hours, the pH of the solution was 2.6. After the acidic wash was removed, the gel weighed 5973.0 g. 75 Kg of neutral saline was then added to the gel, and the gel was further agitated with nitrogen for 4 hours. 94.2 g of 1 M sodium hydroxide was then added thrice to the solution at 4, 6 and 8 hours after the start of the wash. The gel was washed for a total of 24 hours. After the wash solution was drained, and the gel weighed 11247.6 g. The wash solution was then changed for 10 mM PBS solution (41 Kg) and the gel was further agitated for 16 hours. The wash solution was then drained and the gel was weighed (13783.6 g). The FPC of the gel at the end of all washing steps was 1.07%. This material was homogenized using a 20 mesh screen. Rheological data of gel are shown in Table 3

EXAMPLE 32

1.0-1.25% Sodium Hyaluronate Solution

This Example illustrates the preparation of a sterile 1.0-1.25% sodium hyaluronate solution.

40.5 g of high MW sodium hyaluronate (HA) powder was placed into a sterile 5 L Biopak® bag. 3420.0 g of 10 mM phosphate buffered saline was added to the HA using a 0.22 µm sterilizing point-of-use filter placed between the pump and the Biopak® bag. The bag was sealed and the contents were agitated at room temperature on a wave table at a speed of 25-35 rpm for 6 days. The rheological datum for this solution is shown Table 3.

EXAMPLE 33

Gel-Fluid 80:20 (w/w) Mixture (Hylastan SGL-80)

This Example illustrates the preparation of hylastan SGL-80.

11200 g of the gel prepared as described in Example 31 and 2800 g of the sodium hyaluronate solution ("fluid") prepared as described in Example 32 from were placed into a sterile 18 L glass vessel. The vessel was capped and shaken for 68 hours on an Inversina® mixer at 25-35 rpm at room temperature. The gel-fluid mixture was then filled into 5 cm$^3$ glass syringes which were then autoclaved at 131° C. for 2.5 minutes. The rheological data of the resulting mixture are shown in Table 3.

EXAMPLE 34

10% IPC with Bacterially Fermented Sodium Hyaluronate Low MW

Examples 34 and 35 illustrate the preparation of a gel suitable for use as a dermal filler. Generally, such gels are prepared from hyaluronan (e.g., bacterially fermented HA) cross-linked with DVS as described in the Examples above. Typically, dermal filler gels have the following characteristics: (a) IPC 8-12%, preferably 10-12%; (b) HA MW 500-2500 KDa, preferably 500-600 KDa; (c) DVS:Pol ratio 1:200 to 1:15, preferably 1:100 to 1:15, e.g., 1:50, 1:60; (d) FPC about 1% to 2.5%. The gels may be washed to equilibrium or otherwise. Preferably, the gels may be acid-washed, but may alternatively be washed in neutral saline.

This Example illustrates the preparation of a gel with an IPC of about 10% and a DVS:Pol ratio of 1:60.

117.1 g of NaCl was added to 891.4 g of 0.2 M NaOH solution, and stirred until dissolved. 107.0 g of low MW (500-600 KDa) bacterially fermented sodium hyaluronate was then added to the mixture with rapid mechanical stirring continuing for 120 minutes. The resulting polymer solution had an IPC of approximately 10%. A DVS solution (1.42 mL of DVS and 3.6 mL of IPA) was then slowly added to the polymer solution by pipette (5x~1 mL) over about one minute. After another 2 minutes of stirring, the reaction mixture was poured into 4 Pyrex® trays (23×28×6.5 cm) and sealed with plastic covers. The reaction mixture was stored at room temperature for 4 hours, resulting in a gel. The gel was then transferred to a plastic container containing 30 Kg of neutral saline and 50 mL of 1 M HCl. The gel was agitated at room temperature by slowly bubbling nitrogen through the wash for 18 hours, at which time the pH of the wash was 2.36. After the acidic wash was removed, the gel weighed 1897.3 g. 30 Kg of neutral saline was added to the container, and the gel was further agitated at room temperature by bubbling nitrogen for an additional 5 hours, at which time pH of the wash solution was 3.34 and 150 mL of 0.2 M sodium hydroxide was added. 17 hours later, the pH of the wash was 3.34 and an additional 200 mL of 0.2 M sodium hydroxide was added. A further 200 mL of 0.2 M sodium hydroxide was added 7 hours later. After the gel was agitated for 17 more hours, the wash pH measured 4.30 and an additional 130 mL of 0.2M sodium hydroxide was added. The gel was agitated for 25 hours, at which time the pH measured 10.35. After the wash was discarded, the gel weighed 6690.8 g. 30 Kg of 0.01 M PBS solution was added to the gel, and the gel was washed for 24 hours. Following the PBS wash, the pH of the gel measured 7.31 and the weight of the gel was 6916.5 g. The wash was discarded and the gel was washed again for 24 hours with 30 Kg of 0.01 M PBS solution. After the final wash was discarded, the gel weighed 6956.6 g and had an average FPC of 1.17%. This material was homogenized using 20, 40, 60 and 60 mesh screens and autoclaved at 126° C. for 10 minutes. The rheological data of this gel are shown in Table 3.

EXAMPLE 35

12% Bacterially Fermented Sodium Hyaluronate Dermal Filler

This Example illustrates the preparation of a gel with an IPC of 12% and a DVS:Pol ratio of 1:50.

23.4 g of NaCl was added to 168.9 g of 0.2 M NaOH solution, and stirred until dissolved. Low MW (500-600 KDa) bacterially fermented sodium hyaluronate (29.4 g) was added to the solution with rapid mechanical stirring which continued for 120 minutes total. The resulting polymer solution had an IPC of approximately 12%. 2 ml of a DVS solution (0.41 mL of DVS dissolved in 1.6 mL of IPA) was added slowly by pipette (5x~0.4 mL) over about 30 seconds. After another 2 minutes of stirring, the reaction mixture was poured into a Pyrex® tray (23×28×6.5 cm), sealed with a plastic cover, and stored at room temperature for 4 hours, resulting in a gel. The gel was transferred to a plastic container containing 3 Kg of neutral saline mixed with 100.1 g of 1 M HCl. The gel was agitated on an orbital shaker at room temperature for 24 hours. The pH of the solution was 2.28. After the wash was discarded, the gel weighed 416.2 g. 6 L of neutral saline was added to the gel, and the gel was agitated for 18 hours. 9.7 mL aliquots of 1 M sodium hydroxide were added to the solution at 0, 2, 4, 6, and 8 hours. The gel was agitated for 24 hours. The pH after the wash measured 6.65. The wash solution was discarded, and the gel was stored at 2-8° C. for 120 hour. The wash solution was then changed for 0.01 M PBS solution (2 L) and the gel was agitated for an additional 21 hours, upon which the wash solution was drained. At this time, the gel weighed 1036.2 g. The FPC of this gel was 2.4%. This material was homogenized using 20, 40, 60, 40, 60, 100 and 200 mesh screens and autoclaved at 126° C. for 10 minutes. The rheological data for this material are shown in Table 3.

EXAMPLE 36

Ultra-Low MW Polymer-Based Gels

Solutions of various ultra low MW HA (<500 KDa) were prepared in 0.2 N NaOH as described in the Examples above. Viscosity was measured with Bohlin C-VOR rheometer at a shear rate of 1 sect$^{-1}$. The relationship between HA MW and 1/IPC for a fixed viscosity value is a directly proportional function as shown in FIG. 4. Therefore, it is expected that in order to achieve desired viscosity, elasticity and softness, the DVS:Pol ratios for gels prepared from ultra low MW range from about 0.0025 to about 20, e.g., about 0.05 to about 20, 0.01 to about 20, depending on the IPC and MW of the polymer.

EXAMPLE 37

Assay for Percent Modification

Basis for Assay

Figure 5A:
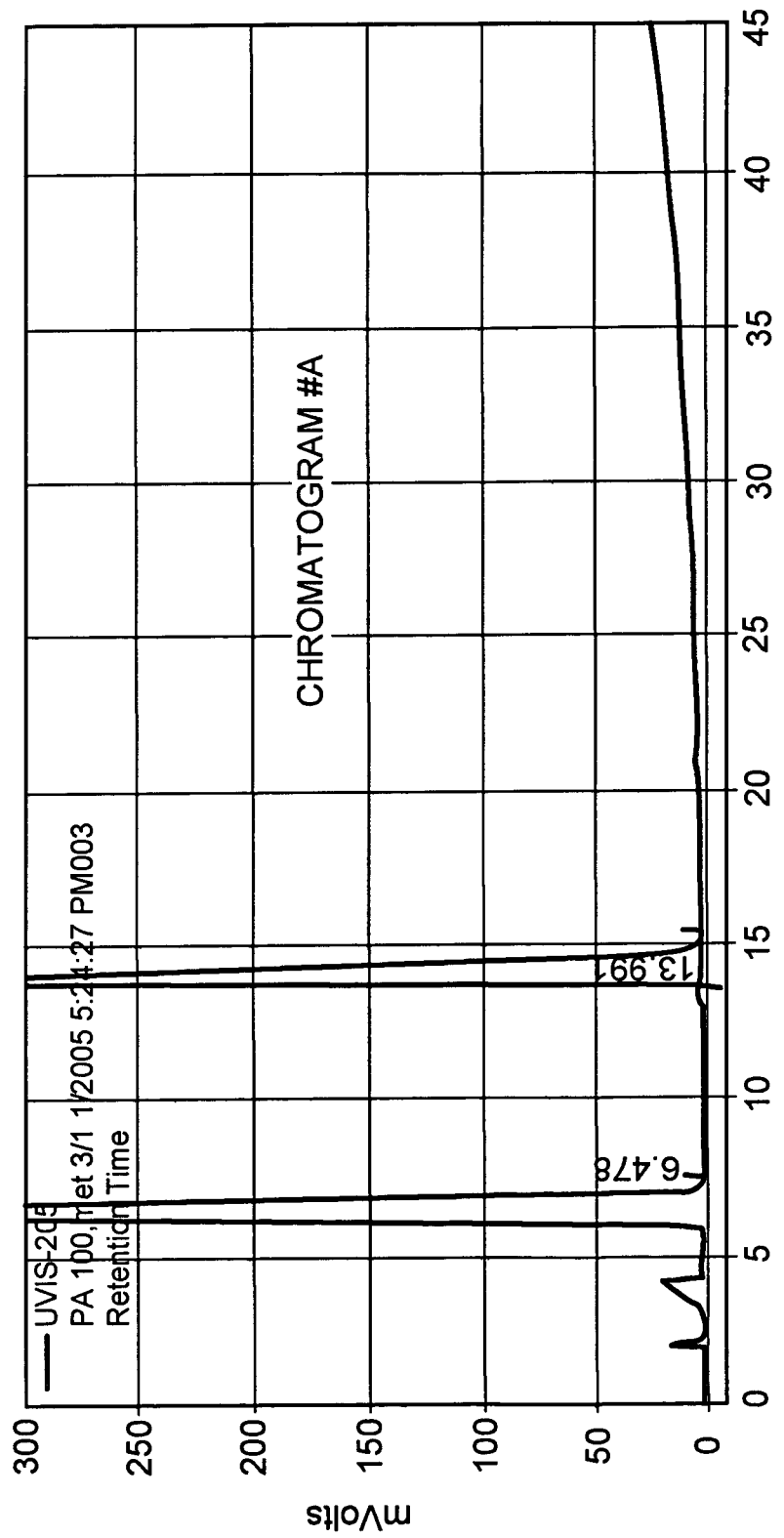
FIG. 5a is a HPLC chromatogram of the complete digestion of a native hyaluronan not subjected a crosslinking reaction showing peaks for tetramer and hexamer fragments.

Numerous publications[Refs 1, 2, 3] report that intrinsic HA (HA recovered from naturally occurring sources), upon the treatment with *Streptomyces hyaluronidase*, yields oligosaccharides with 4,5-unsaturated glucuronosyl residues at the non-reducing end. It is known that a complete digestion of unmodified HA results in only two final digestion products: the tetrasaccharide and hexasaccharide (See FIG. 5A).[Refs 1, 2, 3] It is found that octasaccharides, either saturated or unsaturated, were substrates of the minimum size for digestion with the enzyme.[Ref 2] Time course studies by HPLC to monitor the degradation of unmodified HA with this specific enzyme digestion demonstrate the separation of oligomers from tetrasaccharide up to 20-unit oligomer (see FIG. 5B).[Ref 1]

An assay has been developed which measures the degree to which HA units in a gel have been modified by a crosslinking agent, such as for DVS (a "% modification" assay). According to the assay, an HPLC chromatogram of an incomplete digestion of unmodified HA was generated to calibrate the chromatographic peaks resulted from a complete digestion of a sample gel. The retention time of the octasaccharide peak from the chromatogram of unmodified HA provides a time reference for a measure of the HA-DVS-HA crosslinked digested fragments. In general we observe that the total % modification of HA in a sample gel increases as the molar ratio of DVS:HA increases. The assay is described in greater detail below. In general, it shows good reproducibility.

Details of Assay

*Streptomyces hyaluronidase* used for digestion was purchased from CalBiochem. A CarboPac PA100 LC column was purchased from Dionex Corp. All gels were first diluted with 100 mM sodium acetate, pH 5.0 buffer solution to a final concentration of 0.4% to ensure an optimal digestion condition. Then the divinyl sulfone modified HA gel was treated with *streptomyces*-derived hyaluronidase to undergo a 3-step hyaluronidase digestion.

All gels were first diluted with 100 mM sodium acetate, pH 5.0 buffer solution to a final concentration of 0.4% to ensure an optimal digestion condition. By employing the charge and size sensitive LC column, and optimizing the mobile phase composition, this specific HPLC method allowed distinct separation between tetramer, hexamer, octamer and decamer and so forth up to a 16-unit oligomer (see FIG. 5B). Moreover, the generation of the 4,5-unsaturated double bond offers UV detection at 232 nm for the assay.

Interpretation of the assay is based on the assumption that any peak eluting after the octamer is the result of a cross-linked fragment. In other words, upon completion of the digestion, the enzyme usually generates two oligosaccharide products from the natural substrate: a tetrasaccharide and a hexasaccharide with delta 4,5-unsaturation at the non-reducing end. Therefore, any digested fragment eluting after the octamer elution time correspond to a fragment possessing eight saccharide units or more indicatings the presence of at least one cross-linked modification in the fragment.

In sum, all peaks eluting later than the octamer are designated as peaks of crosslinked fragments, and the percentage of the combined peak area is assigned as the % crosslink modification. Any peak eluting after tetramer peak and before the hexamer peak is designated as tetramer plus, and is presumptively indicative of pendant modification of HA (wherein the crosslinker has reacted with only one strand of HA and has not formed a crosslink with a second strand). Any peak eluting between the hexamer and octamer peaks is designated as hexamer plus, and is indicative of pendant modification of HA. The combined % peak area of tetramer plus and hexamer plus provides the % pendant modification.

Since the integrated peak area is proportional to the concentration of the fragment, the relative percent modification of each type (i.e., pendant or crosslink) was determined based upon the ratio of the area percentage of the peak representing each type of modification over the total area of all the peaks in the chromatogram. The % pendant modification is calculated by the ratio of the sum of the area peaks for the tetramer plus and hexamer plus over the sum of the total area of all the peaks. The % crosslink modification is calculated by the ratio of the sum of the area peaks of the octamer plus, decamer plus and beyond over the total area of all the peaks. The total % modification is the sum of the % pendant and % crosslink.

The peak identification, retention time, calculation of percentage from peak area and area percent of complete digest of HA, incomplete digest of HA and sample gel (from Example 35) are presented in Tables 5, 6 and 7, below.

Upon the completion of enzyme digestion of HA, the two peaks are shown in Chromatogram #A (FIG. 5a), a tetramer peak and a hexamer peak. The former contributes approximate 58% of combined peak area. The later contributes 42% of the combined peak area. (Table #5).

Figure 5B:
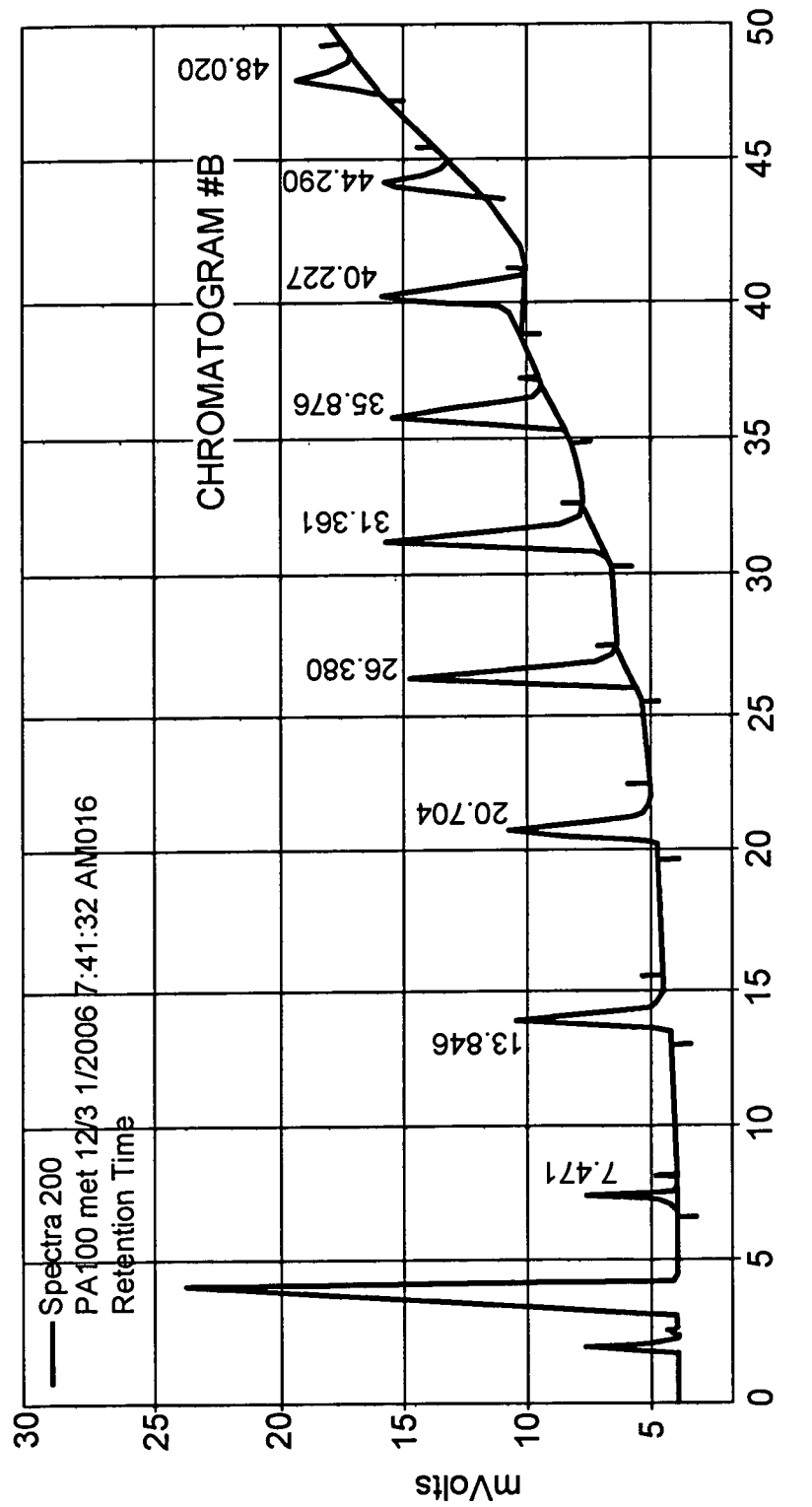
FIG. 5b is a HPLC chromatogram of the incomplete digestion of a native hyaluronan not subjected a crosslinking reaction showing peaks for tetramer, hexamer and octamer fragments.

The calibration standard chromatogram for the assay is shown as Chromatogram #B (FIG. 5b). It consists of multiple HA fragment peaks assigned as follows: tetramer, hexamer, octamer, decamer, dodecamer and so forth up to a hexadecamer. Their retention times are listed in Table #6.

Figure 5C:
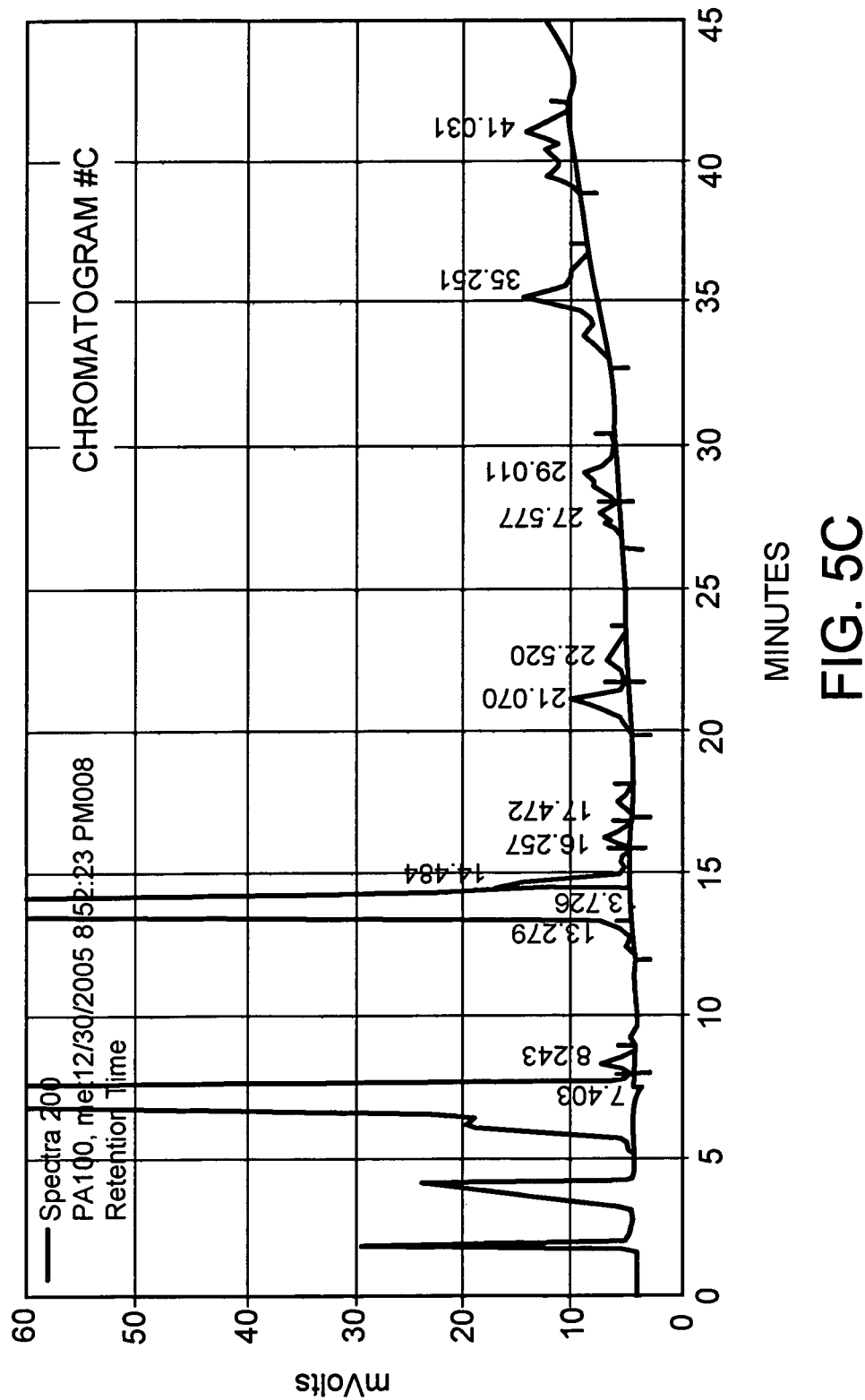
FIG. 5c is a HPLC chromatogram of the complete digestion of a gel subjected to DVS crosslinking reaction according to Example 35, showing peaks of the unmodified tetramer and hexamer fragments, as well as peaks of the corresponding modified fragments: tetramer+ and hexamer+ for pendant modified tetramer and hexamer fragments respectively, and octamer+ for crosslink modified fragments comprising at least eight sugar subunits.

Table 7 provides the retention time, peak area and results derived from them as described above, for a DVS/HA gel made according to Example 35, prepared from 12% IPC, a DVS/HA ratio of 1/50, and having total % pendant chains=2.1%; total % cross linked chains=6.8% (ratio=0.31); and total modification 8.9%. This gel is also reported in row 3 of Table 9. Results are shown in Chromatogram C (corresponding to Table 7) as FIG. 5C.

REFERENCES

1. F. Maccari, F. Tripodi, N. Volpi, High-performance capillary electrophoresis separation of hyaluronan oligosaccharides produced by *Streptomyces hyaluroyticus* hyaluronate lyase, Carbohydrate Polymers 56 (2004) 55-63.
2. E. Shimada, G. Matsumura, Degradation process of hyaluronic acid by *Streptomyces hyaluronidase*, J. Biochem. 88 (1980) 1015-1023
3. L. E. Chun, T. J. Koob, D. R. Eyre, Quantitation of Hyaluronic Acid in Tissues by Ion-Pair Reverse-Phase High-Performance Liquid Chromatography of Oligosaccharide Cleavage Products, Analytical Biochemistry 171 (1988) 197-206

Table 8 shows results of the above assay analysis conducted on acid wash versus neutrally washed prepared gels, using the same Example numbers that are used in Table 2 and in this patent application.

Tables 9-10 below represent the results of the above assay analysis performed on the gels whose synthesis is described in each of the Examples indicated therein.

TABLE 1

Acid Washed Gel Rheology

| Example (autoclave cycle) | IPC % | FPC % | Polymer Source | DVS:Pol w/w | G* Pa (1 Hz) | δ° | Yield Strain | η Pas (sec$^{-1}$) |
|---|---|---|---|---|---|---|---|---|
| 1 (131° C. 10 min) | 0.75 | 0.72 | MMW Bac | 2:1 | 21.6 / 4 | 28 / 59 | 7.5 / 2.9 | 40 / 1.3 |
| 2 (131° C. 10 min) | 0.5 | 0.45 | Hylan | 4:1 | 10.6 / 2.8 | 29.4 / 52.1 | 16 / 2.2 | 28 / 1.1 |
| 3 (131° C. 10 min) | 0.38 | 0.35 | Hylan | 6:1 | 5.2 / 2.2 | 31 / 49 | 14.6 / 2.5 | 13 / 0.7 |
| 4 | 0.25 | — | Hylan | 8:1 | G' (5 Hz) 9 | 24 (5 Hz) | — | — |
| 5 | 0.15 | — | Hylan | 17.7:1 | — | — | — | — |
| 6 (126° C. 10 min) | 4.0 | 0.81 | MMW Bac | 1:17 | 52 / 18 | 10 / 23 | 0.74 / 6.3 | 90 / 56 |
| 7 (121° C. 15 min) | 4.8 | 0.53 | MMW Bac | 1:48 | 33 / 21 | 22 / 27 | 2.5 / 9.3 | 68 / 50 |
| 8 126° C. 10 min | 4.8 | 0.73 | HMW Bac | 1:96 | 38 / 26 | 11 / 15 | 1.4 / 2 | 55 / 45 |
| 9 126° C. 10 min | 5.6 | 0.75 | HMW Bac | 1:48 | 137 / 107 | 2.5 / 2.6 | 0.2 / 0.3 | 70 / 63 |
| 10 126° C. 10 min | 5.6 | 0.74 | HMW Bac | 1:96 | 81 / 54 | 5.4 / 7.3 | 0.5 / 0.8 | 76 / 71 |
| 11 126° C. 10 min | 6.0 | 0.68 | HMW Bac | 1:48 | 109 / 73 | 8 / 9 | 0.1 / 0.1 | 36 / 21 |
| 12 126° C. 10 min | 6.0 | 0.74 | HMW Bac | 1:96 | 94 / 66 | 3 / 3.6 | 0.4 / 0.5 | 58 / 53 |
| 13 126° C. 10 min | 8.0 | 0.81 | MMW Bac | 1:100 | 97.6 / 111 | 19 / 6 | 0.04 / 0.06 | 11 / 9 |

TABLE 2

Comparison of Acid and Neutral Washed Gel Rheology

| Example (autoclave cycle) | IPC % | FPC % | Gel Type | DVS:Pol w/w | G* Pa (1 Hz) | δ° (1 Hz) | Yield Strain | η Pas (1 sec$^{-1}$) |
|---|---|---|---|---|---|---|---|---|
| 14 (126° C. 10 min) | 3.0 | 0.49 | neutral wash | 1:4.25 | 141 / 131 | 8 / 5 | 0.04 / 0.06 | 16 / 14 |
| 15 (126° C. 10 min) | 3.0 | 0.52 | acid wash | 1:4.25 | 115 / 82 | 4.8 / 4.6 | 0.08 / 0.1 | 22 / 15 |
| 16 (126° C. 10 min) | 1.0 | 0.42 | neutral wash | 5:1 | 126 / 65 | 1.7 / 3.4 | 0.3 / 0.3 | 68 / 40 |
| 17 (126° C. 10 min) | 0.9 | 0.49 | acid wash | 5:1 | 47 / 28 | 2.4 / 5 | 0.3 / 1.4 | 54.5 / 43 |
| 18 (126° C. 10 min) | 1.0 | 0.50 | neutral wash | 1.4:1 | 23 / 47 | 6.5 / 13 | 0.5 / 1.4 | 48 / 39 |
| 19 (126° C. 10 min) | 0.9 | 0.49 | acid wash | 1.4:1 | 11 / 2.4 | 25 / 46 | 8 / 20 | 22 / 3 |
| 6 (126° C. 10 min) | 4.0 | 0.81 | acid wash | 1:17 | 52 / 18 | 10 / 23 | 0.74 / 6.3 | 90 / 56 |
| 20 (126° C. 10 min) | 4.0 | 0.63 | neutral wash | 1:15 | 149 / 195 | 4 / 4 | 0.1 / 0.1 | 26 / 21 |
| 21 (a) (126° C. 10 min) | 8.0 | 1.73 | acid wash | 1:17.5 | 1894 / 1892 | 6 / 5 | 0.01 / 0.02 | 60 / 68 |
| 21 (b) (126° C. 10 min) | 8.0 | 1.50 | acid wash | 1:17.5 | 1233 / 902 | 14 / 9 | 0.02 / 0.01 | 36 / 31 |
| 22 (126° C. 10 min) | 8.0 | 1.76 | neutral wash | 1:15 | 2030 / 1870 | 6 / 6 | 0.02 / 0.04 | 67 / 80 |

TABLE 3

Rheological Properties Of Gels And Gel Slurries

| Example | G' Pa (5 Hz) | δ (°) | η Pas (1 sec$^{-1}$) |
|---|---|---|---|
| 31 | 84 | 20 | — |
| 32 | — | — | 47 |
| 33 | 102 | 17 | 98 |
| 34 | 967 | 8 | — |
| 35 | 3079* (*1 Hz) | 12 | 185 |

TABLE 4

Viscosity of Ultra Low MW HA Solutions of Various IPC and MW

| MW (kDa) | IPC (w %) | η Pas (1 sec$^{-1}$) |
|---|---|---|
| 15 | 50 | 20 |
| 60 | 35 | 54 |
| 130 | 29 | 74 |
| 500 | 11 | 730 |

TABLE #5

Complete digest of HA

| Peak Name | Retention Time (min) | peak area | Area Percent |
|---|---|---|---|
| Tetramer | 6.478 | 15304695 | 58.4% |
| Hexamer | 13.991 | 10900996 | 41.6% |

TABLE #6

Incomplete digest of HA

| Peak Name | Retention Time (min) | peak area | Area Percent |
|---|---|---|---|
| Tetramer | 7.471 | 43831 | 2.0% |
| Hexamer | 13.846 | 186447 | 8.5% |
| Octamer | 20.704 | 199556 | 9.1% |
| Decamer | 26.380 | 307031 | 14.0% |
| 12 unit oligomer | 31.361 | 316929 | 14.4% |
| 14 unit oligomer | 35.876 | 249506 | 11.4% |
| 16 unit oligomer | 40.227 | 257313 | 11.7% |
| 18 unit oligomer | 44.290 | 132595 | 6.0% |
| 20 unit oligomer | 48.020 | 117731 | 5.4% |

TABLE #7

Gel according to Example 35

| Peak Name | Retention Time (min) | Peak area | Area Percent | % pendant modification | % crosslink modification |
|---|---|---|---|---|---|
| Tetramer | 7.403 | 11070818 | 55.6% | | |
| Tetramer plus | 8.243 | 64539 | 0.3% | 0.5% | |
| Tetramer plus | 13.279 | 43674 | 0.2% | | |
| Hexamer | 13.726 | 7098936 | 35.6% | | |
| Hexamer plus | 14.484 | 220827 | 1.1% | 1.6% | |
| Hexamer plus | 16.257 | 52899 | 0.3% | | |
| Hexamer plus | 17.472 | 34535 | 0.2% | | |
| Cross-linked | 21.070 | 192493 | 1.0% | | 6.8% |
| Cross-linked | 22.520 | 92251 | 0.5% | | |
| Cross-linked | 27.577 | 51794 | 0.3% | | |
| Cross-linked | 29.011 | 157873 | 0.8% | | |
| Cross-linked | 35.251 | 496134 | 2.5% | | |
| Cross-linked | 41.031 | 350135 | 1.7% | | |
| Total peak area/% | | 19926908 | 100% | 2.1% | 6.80% |

Ratio (P/C) = 2.1/6.8 = 0.31
Total % modification = 2.1% + 6.8% = 8.9%

TABLE 8

Comparison of acid wash to neutral wash

| Example# | washing | Description | % pend. | % cross | Ratio(P/C) | Total % | G* (1) | δ (1) | FPC % |
|---|---|---|---|---|---|---|---|---|---|
| 14 | neutral | 3.0% IPC, DVS/HA = 1/4.25 | 10.42 | 13.07 | 0.80 | 23.49 | 141 | 8 | 0.49 |
| 15 | acid | 3.0% IPC, DVS/HA = 1/4.25 | 10.74 | 12.98 | 0.83 | 23.72 | 115 | 4.8 | 0.52 |
| 16 | neutral | 1.0% IPC, DVS/HA = 5 | 25.03 | 10.02 | 2.50 | 35.05 | 126 | 1.7 | 0.42 |
| 17 | acid | 0.9% IPC, DVS/HA = 5 | 22.26 | 9.75 | 2.28 | 32.01 | 47 | 2.4 | 0.49 |
| 18 | neutral | 1.0% IPC, DVS/HA = 1.4 | 17.50 | 12.76 | 1.37 | 30.26 | 23 | 6.5 | 0.5 |
| 19 | acid | 0.9% IPC, DVS/HA = 1.4 | 16.00 | 12.00 | 1.33 | 28.00 | 11 | 25 | 0.49 |
| 22 | neutral | 8.0% IPC, DVS/HA = 1/15 | 2.61 | 11.92 | 0.22 | 14.53 | 2030 | 6 | 1.76 |
| 21 | acid | 8.0% IPC, DVS/HA = 2/35 | 2.57 | 12.07 | 0.21 | 14.64 | 1894 | 6 | 1.73 |
| 20 | neutral | 4% IPC, DVS/HA = 1/15 | 3.52 | 4.33 | 0.81 | 7.85 | 149 | 4 | 0.63 |
| 6 | acid | 4% IPC, DVS/HA = 1/17 | 4.12 | 3.98 | 1.04 | 8.10 | 52 | 10 | 0.81 |

TABLE 9

Dermal Filler Gel Examples

| Example | Description | % pendant | % cross | Ratio(P/C) | Total % mod. |
|---|---|---|---|---|---|
| 34 | 10% IPC, DVS/HA = 1/60 | 1.8 | 4.9 | 0.37 | 6.7 |
| 35 | 12% IPC, DVS/HA = 1/50 | 1.5 | 4.9 | 0.31 | 6.4 |
| 35 | 12% IPC, DVS/HA = 1/50 | 2.1 | 6.7 | 0.31 | 8.8 |
| 35 | 12% IPC, DVS/HA = 1/50 | 1.0 | 8.0 | 0.13 | 9.0 |
| 35 | 12% IPC, DVS/HA = 1/50 | 1.1 | 8.3 | 0.13 | 9.4 |
| 35 | 12% IPC, DVS/HA = 1/50 | 1.2 | 8.1 | 0.15 | 9.3 |

TABLE 10

Other Gel Examples

| Example# | Description | % pend. | % cross | Ratio(P/C) | % Mod. |
|---|---|---|---|---|---|
| 2 | 0.5% IPC, DVS/HA = 4/1 | 20.04 | 10.69 | 1.87 | 30.73 |
| 3 | 0.38% IPC, DVS/HA = 6/1 | 19.71 | 11.42 | 1.73 | 31.13 |
| 6 | 4% IPC, DVS/HA = 1/17 | 4.12 | 3.98 | 1.04 | 8.10 |
| 7 | 4.8% IPC, DVS/HA = 1/48 | 1.80 | 1.92 | 0.94 | 3.72 |
| 8 | 4.8% IPC, DVS/HA = 1/96 | 1.09 | 2.58 | 0.42 | 3.67 |
| 9 | 5.6% IPC, DVS/HA = 1/48 | 2.48 | 4.69 | 0.53 | 7.17 |
| 10 | 5.6% IPC, DVS/HA = 1/96 | 0.85 | 2.60 | 0.33 | 3.45 |
| 11 | 6.0% IPC, DVS/HA = 1/48 | 1.89 | 4.32 | 0.44 | 6.21 |
| 12 | 6.0% IPC, DVS/HA = 1/96 | 1.6 | 2.96 | 0.54 | 4.56 |
| 13 | 8.0% IPC, DVS/HA = 1/100 | 2.53 | 2.74 | 0.92 | 5.27 |
| 14 | 3.0% IPC, DVS/HA = 1/4.25 | 10.42 | 13.07 | 0.80 | 23.49 |
| 15 | 3.0% IPC, DVS/HA = 1/4.25 | 10.74 | 12.98 | 0.83 | 23.72 |

What is claimed is:

1. A soft cohesive gel composition comprising hyaluron polymer strands, hylan polymer strands or both, said gel composition further comprising divinyl sulfone (DVS) cross-links connecting said polymer strands, said gel being characterized by:
 a. total modification of about 10% or less; and
 b. ratio of pendant groups to cross links in the range from about 1.0 to about 0.10.

2. The composition of claim 1 made by the process of reacting a mixture comprising hyaluron, hylan or a mixture thereof at an initial polymer concentration (IPC) of at least 4% and DVS at a DVS:polymer ratio of less than 0.059.

3. The composition of claim 2 in which the IPC is between 4-12%.

4. The composition of claim 2 in which the DVS:polymer ratio is from 0.021 to about 0.01.

5. The composition of claim 2 in which the polymer strands in the polymer gel have an average molecular weight in the range of 500 KDa to 600 KDa.

6. The composition of claim 1 in which the ratio of pendant groups to cross links is in the range from 0.10 to 0.40.

7. The composition of claim 1 in which the polymer strands in the polymer gel have an average molecular weight from 2.7 MDa to 10 MDa.

8. A cohesive gel composition comprising a hyaluron polymer strands, hylan polymer strands, or both hyaluron polymer strands and hylan polymer strands, said strands being cross-linked with divinyl sulfone (DVS), said gel being characterized by:
 a. total modification of about 25% to 35%;
 b. ratio of pendant groups to cross links of about 1.3 to about 2.5.

9. The composition of claim 8 in which the ratio of pendant groups to cross links is in the range from about 1.5 to about 2.0.

10. A device or pharmaceutical composition comprising the gel composition of claim 1 or claim 8.

11. The device or the pharmaceutical composition of claim 10 further comprising a biologically active material selected from the group consisting of pharmacological drug, a protein, a DNA, a vitamin, or cells.

12. A method of treating osteoarthritis in a patient in need thereof comprising administering the pharmaceutical composition of claim 10 to the patient.

13. The method of claim 12, wherein the composition is administered in a joint space.

14. A method of creating an embolism in a patient in need thereof comprising administering the pharmaceutical composition of claim 10 to the patient to create an embolism.

15. A method of soft tissue augmentation in a patient in need thereof comprising administering the composition of claim 10 to the patient's soft tissue.

16. A method of treating post surgical adhesion in a patient in need thereof comprising administering the pharmaceutical composition of claim 10 to a surgical site of the patient.

17. The device or the pharmaceutical composition of claim 10 further comprising a biologically active material selected from the group consisting of pharmacological drug, a protein, a DNA, a vitamin, and cells.

* * * * *

UNITED STATES PATENT AND TRADEMARK OFFICE
CERTIFICATE OF CORRECTION

PATENT NO. : 8,524,213 B2
APPLICATION NO. : 11/475850
DATED : September 3, 2013
INVENTOR(S) : Adelya K. Leshchiner et al.

Page 1 of 1

It is certified that error appears in the above-identified patent and that said Letters Patent is hereby corrected as shown below:

In the Claims

Column 36, line 24, claim 8, delete "of" and insert -- in the range from --.

Signed and Sealed this
Twelfth Day of November, 2013

Teresa Stanek Rea
*Deputy Director of the United States Patent and Trademark Office*

UNITED STATES PATENT AND TRADEMARK OFFICE
CERTIFICATE OF CORRECTION

PATENT NO. : 8,524,213 B2  
APPLICATION NO. : 11/475850  
DATED : September 3, 2013  
INVENTOR(S) : Adelya K. Leshchiner et al.

Page 1 of 2

It is certified that error appears in the above-identified patent and that said Letters Patent is hereby corrected as shown below:

In the Specification

In column 1, line 61, delete "innulin" and insert -- inulin --, therefor.

In column 3, line 33, delete "opthalmic" and insert -- ophthalmic --, therefor.

In column 3, line 39, delete "arrythmics" and insert -- arrhythmics --, therefor.

In column 4, line 29, delete "Theological" and insert -- rheological --, therefor.

In column 6, line 11, delete "mutiangle" and insert -- multiangle --, therefor.

In column 15, line 54, delete "Theological" and insert -- rheological --, therefor.

In column 19, line 15, delete "Theological" and insert -- rheological --, therefor.

In column 24, line 61, delete "arrythmic" and insert -- arrhythmic --, therefor.

In column 24, line 67, delete "Turbular" and insert -- Turbula --, therefor.

In column 25, line 24, delete "Turbular" and insert -- Turbula --, therefor.

In column 26, line 58, after "3" insert -- . --.

In column 28, line 59, delete "C-VOR" and insert -- CVOR --, therefor.

In column 28, line 60, delete "sect$^{-1}$." and insert -- sec$^{-1}$. --, therefor.

Signed and Sealed this  
Twenty-first Day of April, 2015

Michelle K. Lee  
*Director of the United States Patent and Trademark Office*

CERTIFICATE OF CORRECTION (continued)
U.S. Pat. No. 8,524,213 B2

In column 30, line 54, after "1023" insert -- . --.

In column 30, line 60, after "206" insert -- . --.